US008114662B2

(12) United States Patent
Clark et al.

(10) Patent No.: US 8,114,662 B2
(45) Date of Patent: Feb. 14, 2012

(54) ION-SELECTIVE QUANTUM DOTS

(75) Inventors: Heather A. Clark, Lexington, MA (US);
Daniel I. Harjes, Cambridge, MA (US);
John M. Dubach, Somerville, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 1153 days.

(21) Appl. No.: 11/888,663

(22) Filed: Jul. 31, 2007

(65) Prior Publication Data
US 2008/0131909 A1 Jun. 5, 2008

Related U.S. Application Data

(60) Provisional application No. 60/834,973, filed on Jul. 31, 2006.

(51) Int. Cl.
*G01N 33/53* (2006.01)
*C12M 1/34* (2006.01)
*B82B 3/00* (2006.01)
*C12Q 1/02* (2006.01)
*C12Q 1/20* (2006.01)

(52) U.S. Cl. ......... 435/288.7; 435/7.1; 435/29; 977/774
(58) Field of Classification Search ............... 435/7.1, 435/29, 288.7; 977/774
See application file for complete search history.

(56) References Cited

U.S. PATENT DOCUMENTS

| 6,143,570 | A * | 11/2000 | Alder et al. ............ 436/74 |
| 2006/0148104 | A1 | 7/2006 | Marini et al. |
| 2007/0107625 | A1 | 5/2007 | Anderson et al. |
| 2009/0142274 | A1 * | 6/2009 | Clark et al. ........... 424/9.6 |
| 2009/0155183 | A1 | 6/2009 | Clark |
| 2010/0221188 | A1 * | 9/2010 | Clark et al. ........... 424/9.6 |
| 2010/0227334 | A1 | 9/2010 | Clark |

FOREIGN PATENT DOCUMENTS

| WO | WO-2004/083902 | 9/2004 |
| WO | WO 2006/050257 | 5/2006 |
| WO | WO-2007054689 | 5/2007 |
| WO | WO-2007/067733 | 6/2007 |
| WO | WO-2007067743 | 6/2007 |
| WO | WO 2008/063151 | 5/2008 |

OTHER PUBLICATIONS

Jia et al., 2002. Method to Construct a Third-Generation Horseradish Peroxidase Biosensor: Self-Assembling Gold Nanoparticles to Three-Dimensional Sol-Gel Network. Analytical Chemistry vol. 74, pp. 2217-2223.*
Püntener et al. 2004.Improving the lower detection limit of potentiometric sensors by covalently binding the ionophore to a polymer backbone. Analytica Chimica Acta, vol. 503, pp. 187-194.*
Chen et al. Lighting up cancer cells with "dots". The Lancet, vol. 364 Dec. 4, 2004, pp. 2001-2003.*
Clapp, et al., "Quantum Dot-Based Multiplexed Fluorescence Resonance Energy Transfer," *J. Am. Chem. Soc.*, 127:18212-18221 (2005).
Goldman, et al., "Multiplexed Toxin Analysis Using Four Colors of Quantum Dot fluororeagents," *Anaytical Chemisrty*, 76(3):684-688 (2004).
Ruedas-Rama, et al., "A multi-ion particle sensor," *Chem. Commun. (Camb)*, 15:1544-1546 (2007).
Snee, et al., "A Ratiometric CdSe/ZnS Nanocrystal pH Sensor," *J. Am. Chem. Soc.*, 128(41):13320-13321 (2006).
Xu, et al., "Multicolor Quantum Dot Encoding for Polymeric Particle-Based Optical Ion Sensors," *Anaytical Chemisrty*, 79(10):3716-3723 (2007).
Dubach, et al., "Ion-Selective Nano-optodes Incorporating Quantum Dots," *J. Am. Chem. Soc.*, 129(27), 8418-8419, (2007).
Buck et al., "Nanoscale Probes Encapsulated by Biologically Localized Embedding (PEBBLEs) for Ion Sensing and Imaging in Live Cells", *TALANTA*, 63:1 pp. 41-59 (2004).
Nagai et al., "Circularly permuted green fluorescent proteins engineered to sense $Ca^{2+}$", *PNAS*, 98(6):3197-3202 (2001).
Clark, H. A., et al., "Optochemical Nanosensors and Subcellar Applications in Living Cells," *Mikrochimica Acta*, 131(1/02):121-128 (1999).
Garg et al., "Micropigmentation: Tattooing for Medical Purposes", *Dermatol Surg.* 31:928-31 (2005).
Kulcu et al., "Physiological Differences Between Interstitial Glucose and Blood Glucose Measured in Human Subjects", *Diabetes Care*, 26(8):2405-09 (2003).
Schmidtke et al., "Measurement and Modeling of the Transient Difference Between Blood and Subcutaneous Glucose Concentrations in the Rat After Injection of Insulin", *Proc. Natl. Acad. Sci. USA*, 95:294-99 (1998).
Tamada et al., "Noninvasive Glucose Monitoring Comprehensive Clinical Results", *JAMA*, 282(19):1839-44 (1999).
Bruchez et al., "Semiconductor Nanocrystals as Fluorescent Biological Labels," 281:2013-2016, (1998).
Springsteen et al., "Alizarin Red S. as a general optical reporter for studying the binding of boronic acids with carbohydrates", The Royal Csociety of Chemistry 17:1608-1609 (2001).

* cited by examiner

*Primary Examiner* — Jon P Weber
*Assistant Examiner* — Kailash C Srivastava
(74) *Attorney, Agent, or Firm* — Ropes & Gray LLP

(57) ABSTRACT

The invention provides ion-selective sensors comprising quantum dots capable of selectively measuring ions, e.g., $Na^+$, $K^+$, $Cl^-$, etc., in various environments, including in the cytosol of a living cell. Quantum dots are attractive probes for microscopy due to their photophysical advantages over fluorescent dyes, including prolonged photostability, brightness and quantum efficiency. In certain embodiments, a sensor comprises one or more quantum dots, a pH-sensitive dye, and optionally an ion-selective component such as an ionophore. These elements may, for example, be disposed in a polymer matrix. In certain embodiments, the sensors may detect ionic analytes by selective ion extraction by the polymer, thereby inducing a pH change within the sensor which in turn changes the absorbance of the pH-sensitive dye. The change of absorbance may in turn attenuate the intensity of detectable emissions, e.g., fluorescence, from the quantum dot by directly absorbing its fluorescence emission.

39 Claims, 10 Drawing Sheets

CALCEIN    ETHIDIUM BROMIDE    NANOSPHERES    OVERLAY

ION-SELECTIVE QUANTUM DOTS

CROSS-REFERENCE TO RELATED CASES

This application claims the benefit of U.S. Provisional Patent Application No. 60/834,973, entitled "Ion-Selective Quantum Dots," filed on Jul. 31, 2006, the entire disclosure of which is hereby incorporated by reference as if set forth herein in its entirety.

BACKGROUND OF THE INVENTION

Ion channels lie at the heart of the dynamics of excitable cells and control the action potential responsible for the beat of a cardiac cell or the firing of a synapse. Traditionally, calcium has been the most studied ion in the intracellular space, and as a result a good deal is understood about calcium ion dynamics, regulation and impact on the cell. While it is generally believed that sodium is essential to the function of excitable cells, its role is not as well understood. Sodium channels occur at sites of action potential generation in neurons and are responsible for the upstroke of the action potential in cardiac cells. Sodium channelopathies are known to be responsible for major classes of disease, including epilepsy and hypertension, as well as leading to potentially fatal arrhythmias in Long QT syndrome. In addition, calcium dynamics are often dependent upon sodium, through the sodium/calcium exchanger. The exchanger is responsible for the rapid export of calcium from the cell and is driven by the transmembrane sodium gradient. While channel labeling studies have elucidated the location of sodium channels, little is known about the function, dynamics and impact of sodium channels.

There is a wide selection of methods for measuring ion flux in cells including, for example, patch clamping, fluorescent indicator dyes, polymer-based ion-selective nanosensors and dye-loaded liposomes. There are, however, disadvantages to the available methods of ion monitoring. For example, whole-cell patch clamp monitoring which involves contacting cells with a pulled glass capillary to electrically monitor ion channels, can be performed on single cells but not reliably in a high-throughput fashion. Fluorescent ion-indicator dyes while effective for monitoring certain ions, lack selectivity for other physiological ions and are easily photobleached. Ion-selective nanosensors (e.g., probes encapsulated by biologically localized embedding (PEBBLEs)) which comprise a fluorescent indicator dye display fast response time to ions as they diffuse into the polymer matrix, however, the components of the nanosensors, such as the fluorescent dye, are also prone to photobleaching. Dye-loaded liposomes are highly biocompatible due to their lipid construction but are limited in their range of detectable analytes particularly to gases.

New methods are needed for monitoring ion fluctuations in cells that are selective for a particular ionic analyte such as sodium, are biocompatible and have prolonged sensor lifespans. Further, sensors that are small enough to enter the cell but emit a strong enough signal to be measured extracellularly would be highly desired.

SUMMARY OF THE INVENTION

The invention provides ion-selective sensors comprising quantum dots capable of selectively measuring ions, e.g., $Na^+$, $K^+$, $Cl^-$, etc., in the cytosol of a single living cell. Quantum dots are attractive probes for microscopy due to their photophysical advantages over fluorescent dyes, including prolonged photostability, brightness and quantum efficiency. In certain embodiments, a sensor comprises one or more quantum dots, a pH-sensitive dye, and optionally an ion-selective component such as an ionophore. These elements may, for example, be disposed in a polymer matrix. In certain embodiments, the sensors may detect ionic analytes by selective ion extraction by the polymer, thereby inducing a pH change within the sensor which in turn changes the absorbance of the pH-sensitive dye. The change of absorbance may in turn attenuate the intensity of detectable emissions, e.g., fluorescence, from the quantum dot by directly absorbing its fluorescence emission.

DETAILED DESCRIPTION OF THE INVENTION

Figure 1:
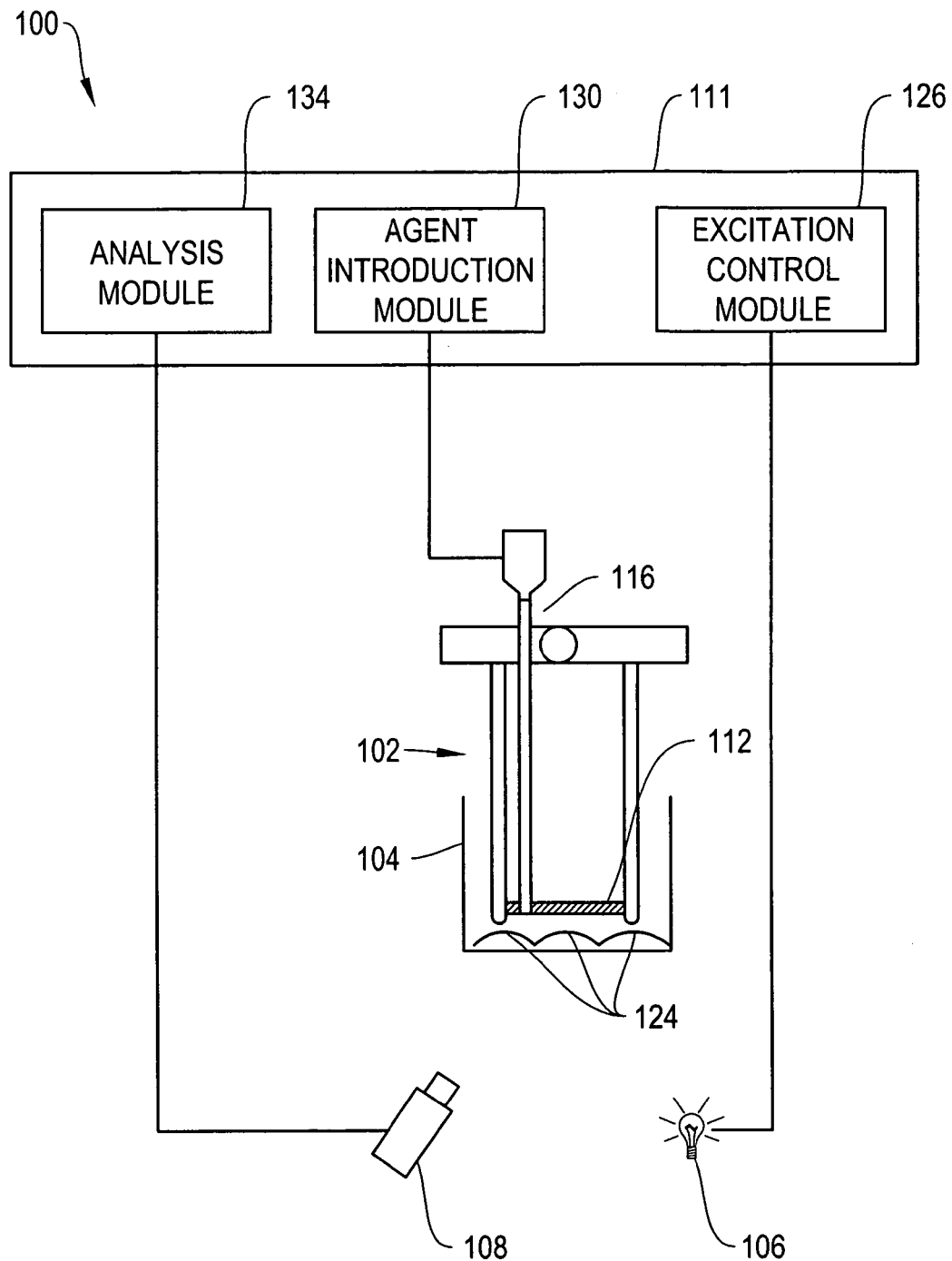
FIG. 1 is a schematic diagram of a cell assay system according to an illustrative embodiment of the invention.

In brief overview, embodiments of the present invention provide systems, methods, and devices for measuring ionic analytes. In exemplary embodiments, sensors are placed inside or outside a cell. Changes in emissions from the sensor indicate the ion concentrations and fluxes from the cell. In certain aspects, the sensors comprise a polymer, a fluorescent semiconductor nanocrystal (also known as a quantum dot™ particle) that fluoresces at a first wavelength, and a chromoionophore that absorbs photons of the first wavelength in one state and does not absorb photons of the first wavelength in a second state. In monitoring ionic analytes, the chromoionophore changes state in response to proton concentration (i.e., the protonated chromoionophore is one state while the deprotonated chromoionophore is a second state). To monitor a specific analyte, an ionophore that selectively associates with specific ions or groups of ions is included in the sensor. Once the ionophore associates with a cationic analyte (e.g., $Na^+$ associates with a $Na^+$-selective ionophore), for example, protons are displaced from the sensor to equilibrate charge, altering the state of the chromoionophore. The fluorescence emitted from the sensor indicates the state of the chromoionophore which correlates to the presence and/or concentration of the ionic analyte. Sensors that use fluorescent dyes instead of quantum dots are disclosed in U.S. patent application Ser. No. 11/522,169, filed Sep. 15, 2006, the disclosure of which is incorporated herein by reference.

In certain embodiments, the sensor includes an ionophore, a chromoionophore, a quantum dot, and optionally one or more additives. The components are typically embedded in a polymer. In certain embodiments, the polymer comprises poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, silicones, polyalkylenes such as polyethylene, polypropylene, and polytetrafluoroethylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, poly (propylene fumarate), polyoxymethylene, poloxamers, poly (ortho)esters, poly(butyric acid), poly(valeric acid), poly (lactide-co-caprolactone), trimethylene carbonate, polyvinylpyrrolidone, and the polymers described in Shieh et al., 1994, J. Biomed. Mater. Res., 28, 1465-1475, and in U.S. Pat. No. 4,757,128, Hubbell et al., U.S. Pat. Nos. 5,654,381; 5,627,233; 5,628,863; 5,567,440; and 5,567,435. Other suitable polymers include polyorthoesters (e.g. as disclosed in Heller et al., 2000, Eur. J. Pharm. Biopharn., 50:121-128), polyphosphazenes (e.g. as disclosed in Vandorpe et al., 1997, Biomaterials, 18:1147-1152), and polyphosphoesters (e.g. as disclosed in Encyclopedia of Controlled Drug Delivery, pp. 45-60, Ed. E. Mathiowitz, John Wiley & Sons, Inc. New York, 1999), as well as blends and/or block copolymers of two or more such polymers. The carboxyl termini of lactide- and glycolide-containing polymers may optionally be capped, e.g., by esterification, and the hydroxyl termini may optionally be capped, e.g., by etherification or esterification. In certain embodiments, the polymer comprises or consists essentially of polyvinyl chloride (PVC), polymethyl methacrylate (PMMA) and decyl methacrylate or copolymers or any combination thereof.

In certain embodiments, the polymer comprises a biocompatible polymer, e.g., selected from poly(caprolactone) (PCL), ethylene vinyl acetate polymer (EVA), poly(ethylene glycol) (PEG), poly(vinyl acetate) (PVA), poly(lactic acid) (PLA), poly(glycolic acid) (PGA), poly(lactic-co-glycolic acid) (PLGA), polyalkyl cyanoacrylate, polyethylenimine, dioleyltrimethyammoniumpropane/dioleyl-sn-glycerol-phosphoethanolamine, polysebacic anhydrides, polyurethane, nylons, or copolymers thereof. In polymers including lactic acid monomers, the lactic acid may be D-, L-, or any mixture of D- and L-isomers. The terms "biocompatible polymer" and "biocompatibility" when used in relation to polymers are art-recognized. For example, biocompatible polymers include polymers that are neither themselves toxic to the host (e.g., a cell, an animal, or a human), nor degrade (if the polymer degrades) at a rate that produces monomeric or oligomeric subunits or other byproducts at toxic concentrations in the host. Consequently, in certain embodiments, toxicology of a biodegradable polymer intended for intracellular or in vivo use, such as implantation or injection into a patient, may be determined after one or more toxicity analyses. It is not necessary that any subject composition have a purity of 100% to be deemed biocompatible. Hence, a subject composition may comprise 99%, 98%, 97%, 96%, 95%, 90% 85%, 80%, 75% or even less of biocompatible polymers, e.g., including polymers and other materials and excipients described herein, and still be biocompatible.

The polymer phase may comprise a plasticizer, such as dioctyl sebacate (DOS), o-nitrophenyl-octylether, dimethyl phthalate, dioctylphenyl-phosphonate, dibutyl phthalate, hexamethylphosphoramide, dibutyl adipate, dioctyl phthalate, diundecyl phthalate, dioctyl adipate, dioctyl sebacate, or other suitable plasticizers. In certain embodiments, the plasticizer is poly(glycerol sebacate), PGS.

In certain embodiments, e.g., particularly where the polymer is biocompatible, a biocompatible plasticizer is used. The term "biocompatible plasticizer" is art-recognized, and includes materials which are soluble or dispersible in the relevant polymer, which increase the flexibility of the polymer matrix, and which, in the amounts employed, are biocompatible. Suitable plasticizers are well known in the art and include those disclosed in U.S. Pat. Nos. 2,784,127 and 4,444,933. Specific plasticizers include, by way of example, acetyl tri-n-butyl citrate (c. 20 weight percent or less), acetyltrihexyl citrate (c. 20 weight percent or less), butyl benzyl phthalate, dibutylphthalate, dioctylphthalate, n-butyryl tri-n-hexyl citrate, diethylene glycol dibenzoate (c. 20 weight percent or less) and the like.

The ionophore is a compound, typically an electrically neutral compound, that associates (e.g., forms a complex, chelate, or other non-covalent association) with a target ion, and is selective for the target ion relative to other ions. The ionophore is selected to be lipid-soluble and does not emit light in the visible spectrum in either of its complexed and non-complexed states. In certain aspects, the ionophore of the mixture included herein is chosen to selectively bind an ionic analyte, for example, $K^+$, $Na^+$, $Ca^{2+}$, $H^+$, $Ba^{2+}$, $Li^+$, $Cl^-$, $NH_4^+$, or $NO_3^-$. Potassium ion ionophores include, for example, valinomycin, crown ethers, e.g., dimethyldibenzo-30-crown-10, dicyclohexyl-18-crown, dimethyldicyclohexyl-18-crown-6, tetraphenyl borate, tetrakis(chlorophenyl) borate. Sodium ion ionophores include, for example, methyl monensin, N,N',N"-triheptyl-N,N',N"-trimethyl-4,4',4"-propylidintris-(3-oxabutyramide), N,N,N',N'-tetracyclohexyl-1, 2-phenylenedioxydiacetamide, 4-octadecanoyloxymethyl-N,N,N',N'-tetracyclohexyl-1,2-phenylenedioxydiacetamide, bis[(12-crown-4)methyl]dodecylmethylmalonate. Exemplary calcium ion ionophores include, for example, bis(didecylphosphate), bis(4-octylphenylphosphate), bis(4-(1,1,3,3-tetramethylbutyl)phenylphosphate tetracosamethylcyclododecasiloxane, N,N'-di(11-ethoxycarbonyl)undecyl)-N,N',4,5-tetramethyl-3,6-dioxaoctane diamide. Barium ion ionophores include, for example, calcium di(2-ethylhexyl)phosphate+decan-1-ol, barium complex of nonylphenoxypoly(ethyleneoxy)ethanol in ortho-nitrodiphenyl ether. Chloride ion ionophores include, for example, {μ-[4,5-dimethyl-3,6-bis(octyloxy)-1,2-phenylene]}bis(trifluoroacetato-O)dimercuri (ETH 9009), {μ-[4,5-dimethyl-3,6-bis(dodecyloxy)-1,2-phenylene]}bis(mercury chloride) (ETH 9033), 5,10,15,20-tetraphenyl-21H,23H-porphin manganese (III) chloride (MnTPPCl), tributyltin chloride (TBTCl) and trioctyltin chloride (TOTCl). Bicarbonate ion ionophores of the invention include, for example, quaternary ammonium ion exchanger p-octodecyloxy-meta-chlorophenyl-hydrazone-mesoxalonitrile. Ammonium ion ionophores include, for example, nonactin and monactin. Nitrate ion ionophores include, for example, tridodecylhexadecylammonium nitrate+n-octyl-ortho-nitrophenyl, 1:10 phenanthroline nickel (II) nitrate+para-nitrocymene. Lithium ion ionophores include, for example, N,N'-diheptyl-N,N',5,5-tetramethyl-3, 7-dioxononanediamide), 12-crown-4,6,6-dibenzyl-14-crown-4.

A chromoionophore is an ionophore that changes its optical properties in the visible spectrum depending on the state of complexation. Chromoionophores for use in sensors are typically proton-sensitive dyes that change absorbance (and fluorescence in many cases) depending on the degree of protonation, although chromoionophores that change absorbance in response to other ions can also be used. The chromoionophores are preferably highly lipophilic to inhibit leaching from the sensor matrix. Suitable chromoionophores include Chromoionophore I (i.e., 9-(Diethylamino)-5-(octadecanoylimino)-5H-benzo[a]phenoxazine), Chromoionophore II (i.e., 9-Dimethylamino-5-[4-(16-butyl-2,14-dioxo-3,15-dioxaeicosyl)phenylimino]benzo[a]phenoxazine) and Chromoionophore III (i.e., 9-(Diethylamino)-5-[(2-octyldecyl)imino]benzo[a]phenoxazine). Chromoionophore II exhibits light absorbance peaks at 520 nm and 660 nm and a fluorescent emission peak at 660 nm. Chromoionophore III has light absorbance peaks at 500 nm and 650 nm and fluorescent emission peaks at 570 nm and 670 nm.

Quantum dots are fluorescent semiconductor nanocrystals having a characteristic spectral emission, which is tunable to a desired energy by selection of the particle size, size distribution and composition of the semiconductor nanocrystal. The emission spectra of a population of quantum dots have linewidths as narrow as 25-30 nm, depending on the size distribution heterogeneity of the sample population, and lineshapes that are symmetric, gaussian or nearly gaussian with an absence of a tailing region. Advantageously, the range of excitation wavelengths of the quantum dots is broad. Consequently, this allows the simultaneous excitation of varying populations of quantum dots in a system having distinct emission spectra with a single light source, e.g., in the ultraviolet or blue region of the spectrum.

In certain embodiments, quantum dots of the sensor described herein are, for example, inorganic crystallites between 1 nm and about 1000 nm in diameter, preferably between about 2 nm and about 50 nm, more preferably about 5 nm to 20 nm, such as about 6, 7, 8, 9, 10, 11, 12, 13, 14, 15, 16, 17, 18, 19, or 20 nm. Such quantum dots include a "core" of one or more first semiconductor materials, and which may be surrounded by a "shell" of a second semiconductor material. A semiconductor nanocrystal core surrounded by a semiconductor shell is referred to as a "core/shell" semiconductor nanocrystal. The surrounded "shell" will most preferably have a bandgap greater than the bandgap of the core material and can be chosen so to have an atomic spacing close to that of the "core" substrate. The core and/or the shell material can be a semiconductor material including, but not limited to, those of the group II-VI (ZnS, ZnSe, ZnTe, CdS, CdSe, CdTe, HgS, HgSe, HgTe, MgTe and the like) and III-V (GaN, GaP, GaAs, GaSb, InN, InP, InAs, InSb, AlAs, AlP, AlSb, AlS, and the like) and IV (Ge, Si, Pb and the like) materials, and an alloy thereof, or a mixture thereof.

In certain aspects, a sensor comprises exactly one quantum dot. In certain embodiments, a sensor comprises more than one quantum dot, for example, 2, 3, 4, or 5 quantum dots. In certain embodiments wherein the sensor comprises more than one quantum dot, the sensor comprises two or more types of quantum dots, each type having a distinct emission wavelength, e.g., independently selected from, for example, 490, 520, 545, 560, 580, 620, 655 nm. The availability of two distinct wavelength emissions (e.g., one or more quantum dots of wavelength 545 nm and one or more quantum dots with emission wavelength of 655 nm) may allow improvements in recording of changes in ion concentration by using the ratio of the two distinct signals. Fluctuations in fluorescence that are common to both signals should theoretically cancel in a ratio. The detectable fluorescence emission of the quantum dot particles may fluctuate depending on variables including number of quantum dots, quantum dot location within the cell, photobleaching, and possible changes in excitation light intensity, all effects that can occur slowly and are not related to ion presence or concentration. Therefore, effects including number of quantum dots, quantum dot location within the cell, photobleaching, and possible changes in excitation light intensity, may be attenuated.

In certain embodiments, the fluorescence signal of the quantum dot may trigger a detectable event within the cell. For example, fluorescence may in turn excite a secondary dye or quantum dot in the particle that easily generates reactive oxygen species (ROS). The ROS would then attack the cell, effectively stimulating necrosis (cell death), which may then be detected either visually or using markers sensitive to cell death. Alternatively, instead of including a secondary component within the particle, another particle may be added to the cell or cell culture. This additional particle may, for example, comprise a photo-degradable polymer membrane. When the primary sensor fluoresces, the emitted light will rupture the secondary particle, releasing its contents. The contents may, for example, be a drug that is therapeutic or apoptotic, e.g., triggering another detectable event.

The sensor may comprise an additive, e.g., to embed charge sites within the polymer phase and/or to help enforce charge neutrality within the sensor 112. For sensors targeting cations, the additive can be any inert and preferably lipophilic component that has a negative charge associated with it. For sensors targeting anions, the additive is positively charged and preferably lipophilic. The additive allows the polymer phase to carry a corresponding amount of oppositely charged particles while maintaining overall charge neutrality of the sensor. The concentration ratio of additive to chromoionophore is preferably 1:1, thereby allowing the chromoionphore to become completely protonated or deprotonated. One suitable additive for sensors targeting negative ions is potassium tetrakis[3,5-bis(trifluoromethyl)phenyl]borate (KTFPB). The lipophilic, anionic component TFPB molecules are retained by the polymer phase, and the potassium ions are either complexed by the ionophore or expelled into the sample solution through diffusion. In one particular implementation, the sensor film is composed of a suspension produced from about 60 mg of DOS, 30 mg of PVC, and up to about 5 mg of additive, ionophore, and chromoionophore.

Figure 2A:
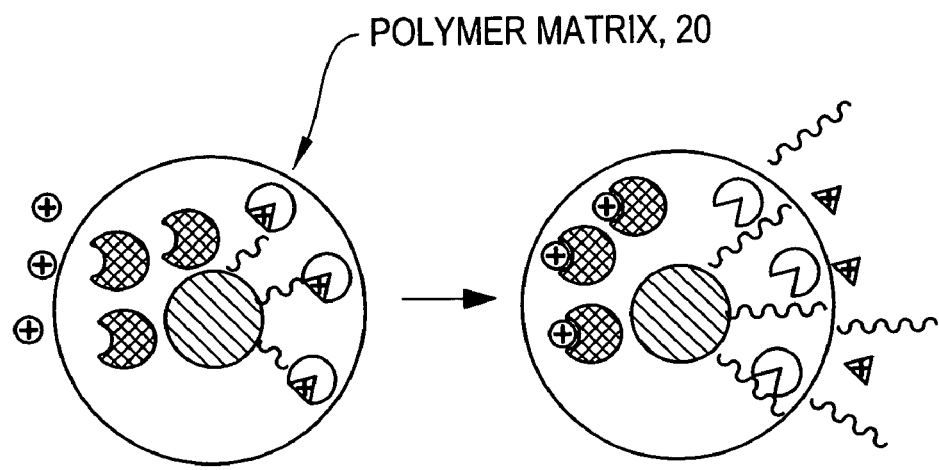
FIG. 2 is a representation of two exemplary modes of operation of the quantum dot incorporated sensor for the detection of cationic analytes. In Mode A, the sensor fluoresces in the presence of the ionic analyte, In Mode B, the sensor fluoresces in the absence of ionic analyte.
Figure 2B:
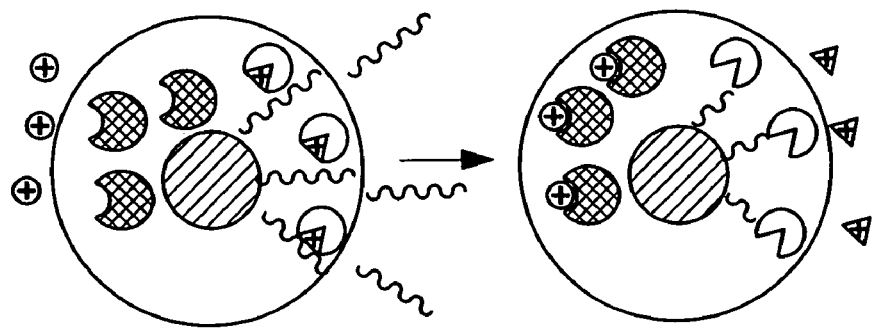

In a sample solution, the sensor continuously extracts or expels, for example, analyte cations depending on ion activity in the sample solution. The ion activity of a sample solution can be monitored by observing the fluorescence of a sensor of the invention in the sample solution. As depicted in FIG. 2, the sensor may fluoresce in the presence of a cationic analyte 21, and not in the absence of said analyte, Mode A. In such embodiments, the chromoionophore 24, of the sensor absorbs photons 25, of a quantum dot 26, when the cationic analyte 21 is not bound to the ionophore 22. In such embodiments, the wavelength of photons 25 emitted from the quantum dot 26 when excited with a light source such as UV or visible light fall within the absorbance range, e.g., maximum absorbance range, of the chromoionophore 24 bound to a proton 23, such that the fluorescence of the quantum dot is attenuated or completely undetectable from outside of the polymer matrix 20 (Mode A, sensor on the left). As the target ion 21 increases in concentration in solution, the ions 21 are drawn into the polymer matrix 20 to bind with the ion-selective ionophore 22. To maintain charge neutrality within the polymer matrix 20, protons 23 dissociate from the chromoionophore 24 in the sensor and diffuse out of the polymer matrix 20 into the sample solution, altering the absorbance properties of the chromoionophore 24. The deprotonated chromoionophore 24 has a shifted absorbance region such that the photons 25 emitted by the quantum dot 26 are no longer absorbed by the chromoionophore 24 (Mode A, sensor on the right). The sensor then emits a detectable signal indicating the presence of the analyte.

In an alternate embodiment for detecting cationic analytes, FIG. 2, Mode B, the quantum dot 27 of the sensor emits photons 25 that are not absorbed by the chromoionophore 24 in the absence of the cationic analyte 21. In certain such embodiments, the chromoionophore 24 absorbs photons 25 of the quantum dot 27 when the cationic analyte 21 is bound to the ionophore 22. In such embodiments, the wavelength of emitted photons 25 from the quantum dot 27 when excited with a light source such as UV or visible light, do not fall within the absorbance range, e.g., the maximum absorbance range, of the chromoionophore 24 when bound to a proton 23, such that the fluorescence of the quantum dot 27 is emitted from the polymer matrix 20 (Mode B, sensor on the left). As the target ion 21 increases in concentration in solution, the ions 21 are drawn into the polymer matrix 20 to bind with the ion-selective ionophore 22. To maintain charge neutrality within the polymer matrix 20 of the sensor, protons 23 dissociate from the chromoionophore 24 of the sensor and diffuse out of the polymer matrix 20 into the sample solution, altering the absorbance properties of the chromoionophore 24. The deprotonated chromoionophore 24 has a shifted absorbance region such that the photons 25 emitted by the quantum dot 27 are absorbed by the chromoionophore 24 (Mode B, sensor on the right). The sensor signal is attenuated or extinguished indicating the presence of the analyte.

Figure 3A:
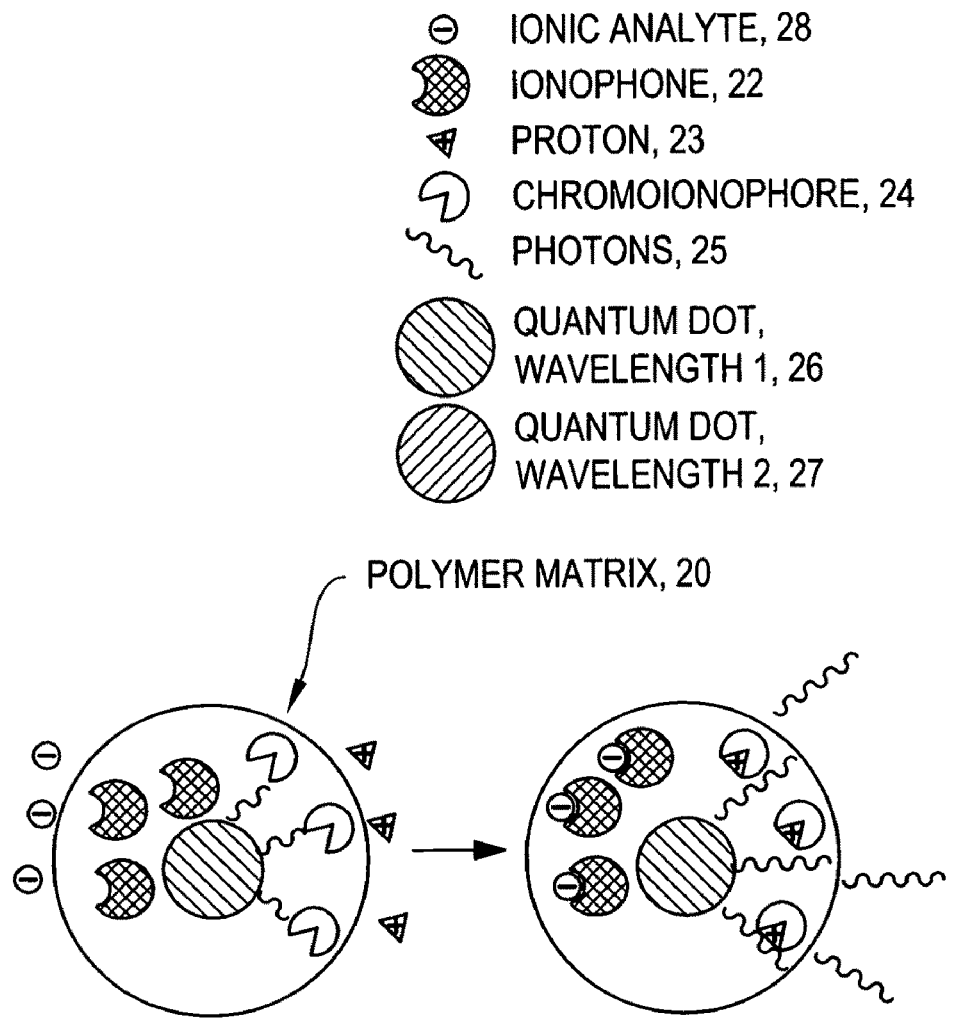
FIG. 3 is a representation of two exemplary modes of operation of the quantum dot incorporated sensor for the detection of anionic analytes. In Mode A, the sensor fluoresces in the presence of the ionic analyte, In Mode B, the sensor fluoresces in the absence of ionic analyte.
Figure 3B:
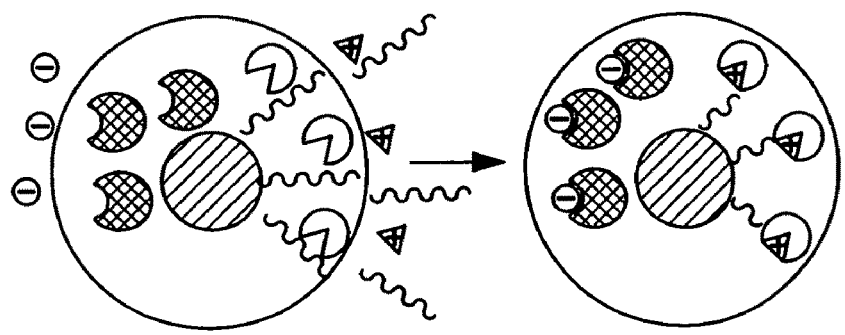

In an embodiment for detecting anionic analytes, depicted in FIG. 3, Mode A, the ionophore 22 of the sensor selectively binds an anionic analyte 28 or a group of anionic analytes. In certain such embodiments, the sensor comprises a chromoionophore 24 which absorbs photons 25 emitted from the quantum dot 26 upon excitation, e.g., by light such as UV or visible, when the ionic analyte 28 is not bound to the ionophore 22 of the sensor. In such a state, the wavelengths of the photons 25 emitted by the quantum dot 26 are within the absorbance range, e.g., the maximum absorbance range, of the chromoionophore 24 in a deprotonated state and the fluorescence detected outside of the polymer matrix 20 is attenuated or undetectable from outside the sensor (FIG. 3, Mode A, sensor on the left). As the target ion 28 increases in concentration in the sample solution, the anionic analyte 28 is drawn into the polymer matrix 20, binding with the ion-selective ionophore 22. To maintain charge neutrality within the polymer matrix 20, protons 23 diffuse from the sample solution into the polymer matrix 20, protonating the chromoionophores 24 such that the absorbance properties are altered. The protonated chromoionophore 24 has a shifted absorbance region such that the photons 25 of the quantum dot 26 are not absorbed by the chromoionophore 24 (FIG. 3, Mode A, sensor on the right). The sensor emits a detectable fluorescence signal indicating the presence of the analyte 28.

In an alternate embodiment for detecting anionic analytes, depicted in FIG. 3, Mode B, the ionophore of the sensor selectively binds an anionic analyte 28 or a group of anionic analytes. In certain such embodiments, the sensor comprises a chromoionophore 24 which does not absorb photons 25 emitted from the quantum dot 26, upon excitation, e.g., by light such as UV or visible, when the ionic analyte 28 is not bound to the ionophore 22 of the sensor. In such a state, the wavelengths of the photons 25 emitted by the quantum dot 26 are outside of the absorbance range, e.g., the maximum absorbance range, of the chromoionophore 24 in a deprotonated state and the fluorescence detected outside of the polymer matrix 20 is attenuated or absent (FIG. 3, Mode B, sensor on the left). As the target ion 28 increases in concentration in the sample solution, the anionic analyte 28 is drawn into the polymer matrix 20, binding with the ion-selective ionophore 22. To maintain charge neutrality in the polymer matrix 20, protons 23 diffuse from the sample solution into the polymer matrix 20, protonating the chromoionophores 24 such that the absorbance properties are altered. The protonated chromoionophore 24 has a shifted absorbance region such that the photons 25 of the quantum dot 26 are not absorbed by the chromoionophore 24 (FIG. 3, Mode B, sensor on the right). The sensor signal is attenuated or extinguished indicating the presence of the analyte 28.

The following is a non-limiting, illustrative list of target ion (21 or 28)/ionophore 22 pairings suitable for use in the sensors: potassium/Potassium Ionophore III (i.e., BME-44, 2-Dodecyl-2-methyl-1,3-propanediyl bis[N-[5'-nitro(benzo- 15-crown-5)-4'-yl]carbamate]), sodium/Sodium Ionophore IV (i.e., 2,3:11,12-Didecalino-16-crown-5 2,6,13,16,19 Pentaoxapentacyclo [18.4.4.4$^{7,12}$.0$^{1,20}$.0$^{7,12}$]dotriacontane), sodium/Sodium Ionophore V (i.e., 4-Octadecanoyloxymethyl-N,N,N',N'-tetracyclohexyl-1,2-phenylenedioxydiacetamide), sodium/Sodium Ionophore VI (i.e., Bis[(12-crown-4)methyl]dodecylmethylmalonate Dodecylmethylmalonic acid bis[(12-crown-4)methyl ester]), sodium/Sodium Ionophore X (4-tert-Butylcalix[4]arene-tetraacetic acid tetraethylester), calcium/Calcium Ionophore III (i.e., Calimycin), and calcium/Calcium ionophore IV (i.e., N,N-Dicyclohexyl-N', N'-dioctadecyl-diglycolic diamide). For target anions, illustrative target ion/ionophore pairings include chloride/Chloride Ionophore III (i.e., 3,6-Didodecyloxy-4,5-dimethyl-o-phenylene-bis(mercury chloride) and nitrite/Nitrite Ionophore I (i.e., Cyanoaqua-cobyrinic acid heptakis(2-phenylethyl ester)).

Figure 4:
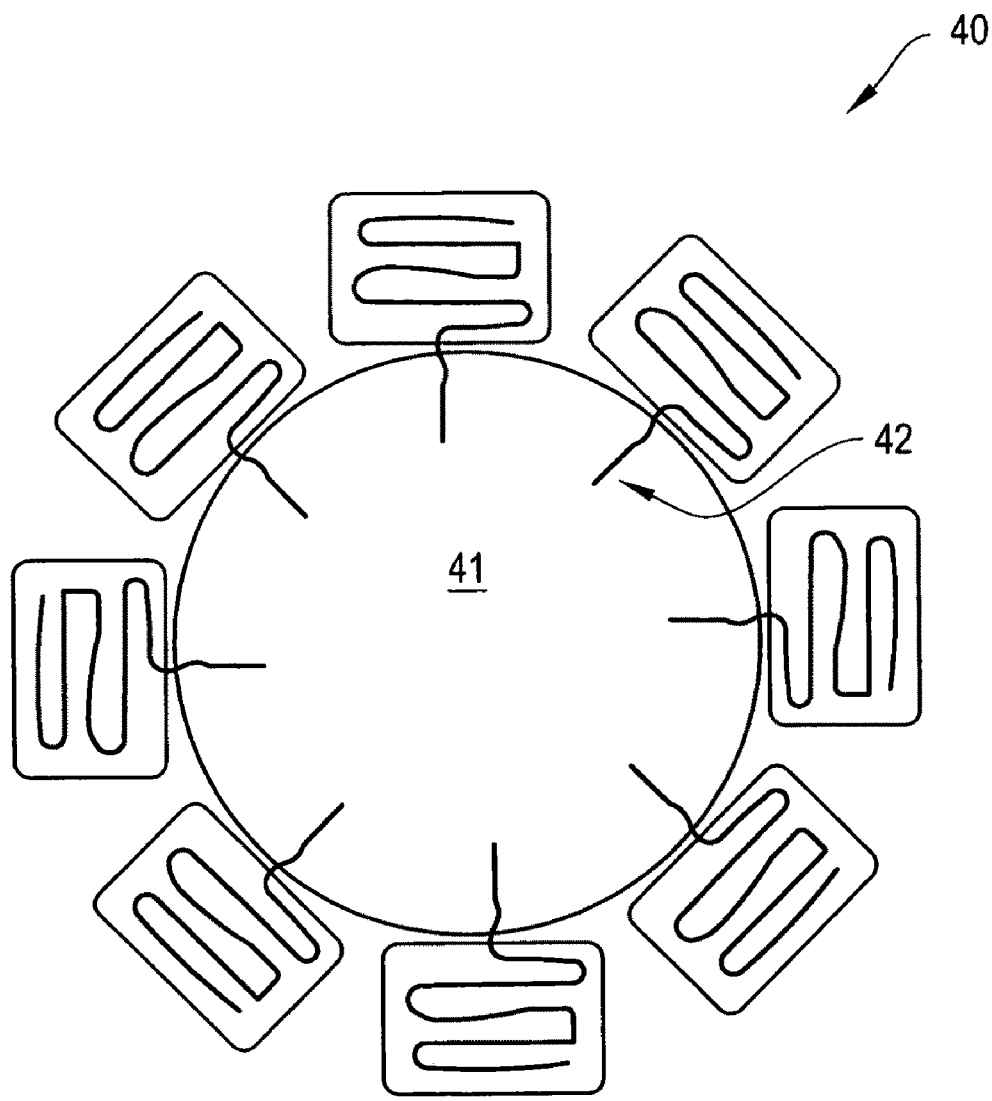
FIG. 4 is a is a representation of a sensor coated with a surface modifier such as PEG.

In certain embodiments, the sensor further comprises a surface modifier (SM). In certain embodiments, the SM comprises a molecule that promotes the delivery or localization of the sensor within a cell. SMs of the invention include molecules with a hydrophilic portion 40 and a hydrophobic portion 42, FIG. 4. In certain embodiments, the hydrophobic portion 42 of the SM anchors the SM to the hydrophobic polymer matrix 41. In certain embodiments, the SM is disposed on the surface of the sensor, e.g., covers a portion of the surface or covers the entire surface. Exemplary hydrophobic portions 42 of the SM include but are not limited to, lipids and hydrophobic polymers. In certain embodiments, the hydrophilic portion 40 of the SM is disposed on the surface of the sensor. An exemplary hydrophilic portion 40 includes, but is not limited to, polyethylene glycol (PEG). In certain embodiments, the hydrophilic portion (PEG) is bound to the hydrophobic portion (lipid) through a linker (e.g., phosphate, ceramide).

In certain embodiments, the sensor further comprises a targeting moiety. In certain embodiments, the targeting moiety is bound to the polymer matrix. In certain embodiments, the targeting moiety is bound to the SM on the surface of the polymer matrix. The targeting moiety, which assists the sensor in localizing to a particular target area, entering a target cell(s), and/or locating proximal to an ion channel, may be selected on the basis of the particular condition or site to be monitored. The targeting moiety may further comprise any of a number of different chemical entities. In one embodiment, the targeting moiety is a small molecule. Molecules which may be suitable for use as targeting moieties in the present invention include haptens, epitopes, and dsDNA fragments and analogs and derivatives thereof Such moieties bind specifically to antibodies, fragments or analogs thereof, including mimetics (for haptens and epitopes), and zinc finger proteins (for dsDNA fragments). Nutrients believed to trigger receptor-mediated endocytosis and therefore useful targeting moieties include biotin, folate, riboflavin, carnitine, inositol, lipoic acid, niacin, pantothenic acid, thiamin, pyridoxal, ascorbic acid, and the lipid soluble vitamins A, D, E and K. Another exemplary type of small molecule targeting moiety includes steroidal lipids, such as cholesterol, and steroidal hormones, such as estradiol, testosterone, etc.

In another embodiment, the targeting moiety may comprise a protein. Particular types of proteins may be selected based on known characteristics of the target site or target cells. For example, the probe can be an antibody either monoclonal or polyclonal, where a corresponding antigen is displayed at the target site. In situations wherein a certain receptor is expressed by the target cells, the targeting moiety may comprise a protein or peptidomimetic ligand capable of binding to that receptor. Proteins ligands of known cell surface receptors include low density lipoproteins, transferrin, insulin, fibrinolytic enzymes, anti-HER2, platelet binding proteins such as annexins, and biological response modifiers (including interleukin, interferon, erythropoietin and colony-stimulating factor). A number of monoclonal antibodies that bind to a specific type of cell have been developed, including monoclonal antibodies specific for tumor-associated antigens in humans. Among the many such monoclonal antibodies that may be used are anti-TAC, or other interleukin-2 receptor antibodies; 9.2.27 and NR-ML-05 to the 250 kilodalton human melanoma-associated proteoglycan; and NR-LU-10 to a pancarcinoma glycoprotein. An antibody employed in the present invention may be an intact (whole) molecule, a fragment thereof, or a functional equivalent thereof. Examples of antibody fragments are F(ab')$_2$, Fab', Fab, and Fv fragments, which may be produced by conventional methods or by genetic or protein engineering.

Other preferred targeting moieties include sugars (e.g., glucose, fucose, galactose, mannose) that are recognized by target-specific receptors. For example, instant claimed constructs can be glycosylated with mannose residues (e.g., attached as C-glycosides to a free nitrogen) to yield targeted constructs having higher affinity binding to tumors expressing mannose receptors (e.g., glioblastomas and gangliocytomas), and bacteria, which are also known to express mannose receptors (Bertozzi, C R and M D Bednarski Carbohydrate Research 223:243 (1992); J. Am. Chem. Soc. 114:2242, 5543 (1992)), as well as potentially other infectious agents. Certain cells, such as malignant cells and blood cells (e.g., A, AB, B, etc.) display particular carbohydrates, for which a corresponding lectin may serve as a targeting moiety.

The nanosensors of the invention can be incorporated into cells to detect ionic analytes and determine the presence and/or concentration, e.g., with a fluorescence signal. FIG. 1 is a schematic diagram of a cell assay system 100 according to an illustrative embodiment of the invention. The cell assay system 100 includes a support 102, a biological sample holder 104, an excitation light source 106, a light sensor 108, and a computing device 111.

The support 102 supports a sensor 112, e.g., a film having a suspension of sensor matrices as described above, for positioning in the biological sample holder 104. In various implementations, the sensor 112 is adhered to the support 102 by deposition in a solution of sensor matrices dissolved or dispersed in a solvent, such as in a polar organic solvent like tetrahydrofuran (THF). In such implementations, the support 102 is preferably formed from a material resistant to the solvent. Materials resistant to THF include, without limitation, 304 stainless steel; 316 stainless steel; acetal polymer (marketed as DELRIN by E.I. du Pont de Nemours and Company); bronze; carbon graphite; carbon steel; ceramic Al$_2$O$_3$, a perfluoroelastomer compound, such as CHEMRAZ marketed by Greene, Tweed; epoxy; HOSTELRY Calloy (marketed by Haynes International, Inc.); KALES elastomer (marketed by DuPont Performance Elastomers); polychlorotrifluoroethylene; NYLON (marketed by E.I. du Pont de Nemours and Company); polyetherether ketone (PEEK); polyphenylene sulfide; and PTFE.

The film of the sensor can be produced in various ways. In one implementation, as described above, a predetermined amount of the sensor mixture (e.g., the combined polymer phase, ionophore, quantum dots, additive, and chromoionophore) is dissolved in a solvent, such as THF. The solution is then deposited, sprayed, or spun onto a surface. The solvent evaporates, leaving the sensor film on the surface.

In another implementation, the film is formed from a deposition of sensor microspheres. To produce the microspheres, a sensor emulsion is formed by injecting a sensor suspension dissolved in THF (e.g., 16 mL THF/100 mg PVC) into a pH buffered solution. The sensor suspension includes approximately 60 mg of DOS, 30 mg of PVC, and up to approximately 5 mg of chromoionophore, additive, and ionophore. The emulsion is then submerged in a sonicating water bath. Typically, 50 µL of the sensor suspension/THF solution is injected into 1,000-1,500 µL of buffered solution. The resulting emulsion contains a mixture of spherical sensor particles ranging in size from 200 nm to 20 pm in diameter. In certain embodiments, the nanosensors range in size from about 5 nm to about 300 nm in diameter, such as about 20 nm to about 200 nm in diameter, e.g., about 100 nm. In certain embodiments, the nanosensors that comprise only one quantum dot range in size from about 5 nm to about 50 nm in diameter, such as about 5 nm to about 25 nm in diameter, e.g., 20 nm. In certain embodiments wherein the particles are non-spherical, the diameter is measured at the widest dimension of the nanosensor. Particles of larger dimension are, of course, readily prepared.

Sensor materials as discussed herein can be sized and shaped in any suitable configuration that can be achieved using the polymer. For example, in certain embodiments, the nanosensors are non-spherical, such as a disk or a cube, or even sculpted or molded into a utilitarian or aesthetic shape. A sensor emulsion can be spun, sprayed, or evaporated onto any surface to create a porous sensor membrane. In certain embodiments, the sensor film can be of a size suitable for the application, such as the coating of a glass slide, the bottoms of wells of a 96-well plate, or even a beverage dispenser, such as a pitcher, tank, or bottle. Films formed from microspheres tend to expose a greater surface area of sensor to a given sample, yielding improved performance characteristics.

In certain aspects, a film of the sensor particles is deposited on the surface of a support. In certain embodiments, the support is an instrument that can be placed in a solution such as a glass rod, a stirring bar, a straw, or glass beads. In certain embodiments, the support is a container in which the ionic solution to be evaluated can be contained. In certain embodiments, the surface of the support is partially coated with the sensor particles while in other embodiments, the support surface is entirely coated with the sensor particles. In certain embodiments, the sensors are incorporated within the support and the support is sculpted into a desired shape such as a stir bar, a film, or a bead.

In certain embodiments, the sensors are used to detect ions in water or other aqueous solutions. In certain embodiments, the support deposited with the sensor particles is used to detect the presence of ions in an aqueous solution. In certain exemplary embodiments, the sensors are used to detect ions in water, e.g., tap water or ground water, to determine the levels of toxic ions in solution or to determine the hardness of the aqueous solution. In certain exemplary embodiments, the sensors are added to manufacturing solutions to measure ions during production of, e.g., the mass production of soda, ion-restoring beverages or other ionic drinks. In certain embodiments, the sensors are used in the laboratory to monitor the ion content of a reaction mixture or stock solution.

The biological sample holder 104 holds a biological sample for analysis by the cell assay system 100. The biological sample can include cells adhered to the walls of the biological sample holder 104, for example, in a monolayer, or cells suspended in a liquid buffer. The biological sample holder 104 is preferably transparent, or at least includes a transparent region through which the sensor 112 can be excited and through which the results of such excitation can be monitored.

The sensor 112 is illuminated with a light source 106 to excite the quantum dots. The light source can be in the UV or visible portion of the electromagnetic spectrum, or the light source may generate a wide spectrum light. In one implementation, the light source 106 is coupled to the support 102.

The emissions of the sensor 112 is detected, e.g., the fluorescence of the sensor is detected by a light sensor 108. The light sensor 108 may include a charge-coupled device, a fluorometer, a photomultiplier tube, or other suitable device for measuring fluorescence. In one implementation, a spectrophotofluorometer is as both the light source 106 and the light sensor 108. The light sensor 108 may also be coupled to the support 102.

The support 102 may include an agent introduction port 118. The agent introduction port 118 can include a pipette or an electro-mechanical dispenser device, such as a solenoid or electrostatically driven plunger or syringe.

The computing device 111 controls the various components of the cell assay system 100. The computing device 111 may be a single computing device or multiple computing devices providing the various functionalities used to control the cell assay system. These functionalities are provided by an excitation control module 126, an agent introduction module 130, and an analysis module 134. The excitation control module 126 controls the light source 108 to emit a wider or narrower wavelength range of excitation light. The agent introduction module 130 controls the introduction of an agent into the biological sample holder 104 via an agent introduction means 118. The analysis module 134 analyzes the output of the light sensor 108, e.g., before and after an agent is introduced into the biological sample holder 104 to determine the effect of the agent on the cells in the biological sample holder 104. The analysis module 134 may also control the other modules in the computing device, i.e., the excitation control module 126 and the agent introduction module 130, to coordinate an assay protocol. The computing device 111 and/or devices may also include various user interface components, such as a keyboard, mouse, trackball, printer, and display.

A module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module. A module of executable code may be a single instruction, or many instructions, and may even be distributed over several different code segments, among different programs, and across several memory devices.

The various modules are in communication with the various devices they control or from which they obtain data. They may be connected over a local area network, wirelessly, over a bus, or over typical cables known in the art of computer interfaces for connecting computing devices with peripherals.

Figure 5A:
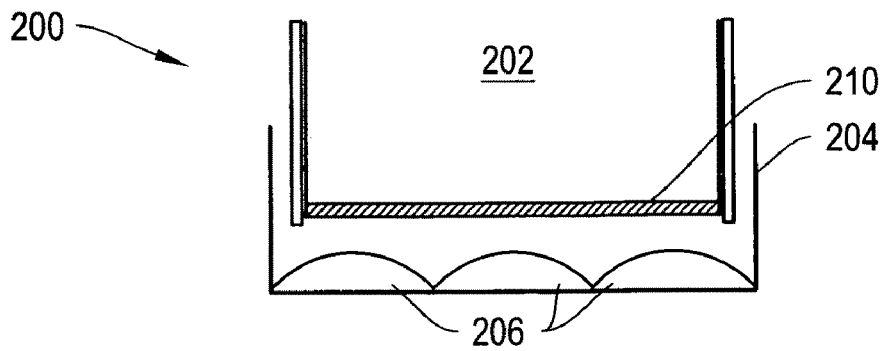
FIG. 5 shows cross sections of various optical sensor arrangements suitable for use in various implementations of a cell assay system: a) optical ion sensor film adhered to a support containing a layer of cells; b) optical ion sensor particles located within cells; c) optical ion sensor film and particles contacting cells from exterior and interior respectively; d) sensor with removable optical sensor film and electrode.

FIGS. 5A-5D depict sensor arrangements suitable for use in various implementations of the cell assay system 100 of FIG. 1. FIG. 5A shows a first sensor arrangement that includes a support 202 and a biological sample holder 204. The biological sample holder 204 includes a monolayer of cells 206 adhered to the biological sample holder 204. Alternatively, the biological sample holder 204 holds cells suspended in a buffer. The support 202 and biological sample holder 204 correspond to the support 102 and biological sample holder 104 of FIG. 1. A sensor film 210 is coupled to the distal end of the support 202.

Figure 5B:
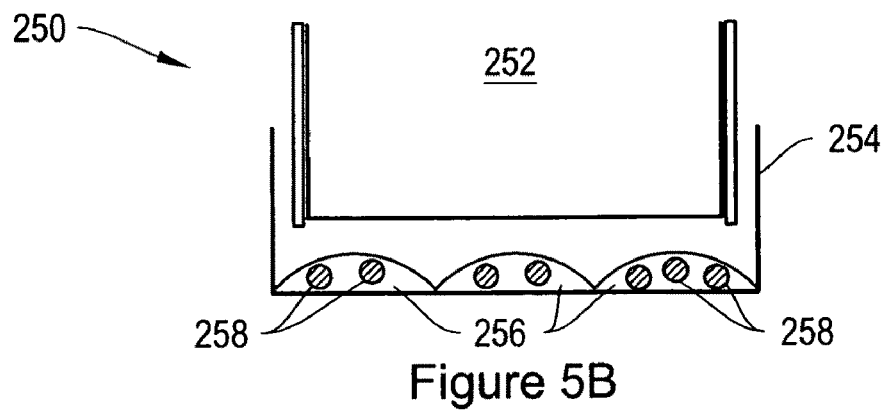

FIG. 5B illustrates an alternative sensor arrangement 250, which includes a biological sample holder 254 having therein a monolayer of cells 256 adhered to the surfaces of the biological sample holder 254, or cells suspended in a buffer. Instead of including a sensor film adhered to a support, the sensor arrangement 250 relies upon nanosensor particles 258 introduced into the cells 256 adhered to the biological sample holder 254.

The nanosensor particles 258 may be introduced into the cells 256 in any suitable manner. In one method, the particles 258 are introduced into a buffer liquid deposited in the biological sample holder 254. A voltage source then generates a voltage sufficiently strong to electroporate the cells 256, thereby allowing the nanosensor particles 258 to enter directly into the cells. In another approach, the surfaces of the nanosensor particles 258 are first coated with a substance such as a hydrophilic coating, for example polyethyleneglycol (PEG), which assist the particles 258 in crossing through cell membranes. The nanosensor particles 258 contact the cells 256 which bring the particles 258 into their interior in vesicles via endocytosis, pinocytosis, phagocytosis, or similar biological processes. In certain embodiments, a substance applied to the nanosensor particles 258 breaks down the vesicle membrane, releasing the nanosensor particles 258 into the cell cytoplasm. In still other approaches, the particles 258 may be introduced into cells 256 using a glass needle or through ballistic bombardment.

To determine compartmentalization of nanosensors within the cells TEM and fluorescence staining can be used. TEM can be used to determine location of the nanosensor in a cell, may provide a good understanding of nanosensor transport in the cell and serve as a validation of the co-localization staining. The second method, co-localization staining, can be used to determine endosomal release.

Dyes suitable for performing co-localization studies include: FM1-43, FM4-64, Fluorescein Transferrin, and Lysotracker Red. FM1-43 is a lipophilic dye that readily stains cell membranes. Previous studies have shown the effectiveness of FM1-43 to stain endosomes. Its fluorescence emission is typically greatly increased upon incorporation into a hydrophobic environment. FM1-43 will typically stain the plasma membrane of a cell and remain associated with the lipid bilayer as it forms an endosome. Dye that is not taken into the cell and remains on the plasma membrane can be easily removed by gentle washing. FM4-64 is an analog of FM1-43 and behaves in a very similar fashion. It is more hydrophobic then FM1-43 and therefore may be more suitable for endocytosis studies. FM4-64 has been well characterized as an endosomal stain. The long wavelength emission of FM4-64 may be advantageous when using sensors of different spectral properties similar to the other fluorescent stains being utilized.

In some embodiments, the sensor is attached to the exterior of a cell rather than introduced into the interior. If, for example, the activity of an ion channel is to be studied, the sensor may be attached to the cell surface or placed in close proximity to the cell surface in a location where ion concentrations are in flux, such as adjacent to an ion channel. The sensor may be positioned adjacent to the ion channel of a cell, for example, by covalently linking one or more antibodies that selectively bind the ion channel of interest to a sensor particle as described above. The antibody-linked sensor particles may be added to a cell suspension to bind to the ion channel. This approach can be used to link ion-specific sensors to any feature on the exterior of the cell membrane to which antibodies selectively bind. Alternatively, the sensors may be attached to the cell membrane by other suitable coupling chemistries, e.g., biotin-(strept)avidin complexing or polysaccharide binding. See the thesis "High Throughput Optical Sensor Arrays for Drug Screening" by Daniel I. Harjes (2006), available from the Massachusetts Institute of Technology and incorporated herein by reference.

Figure 5C:
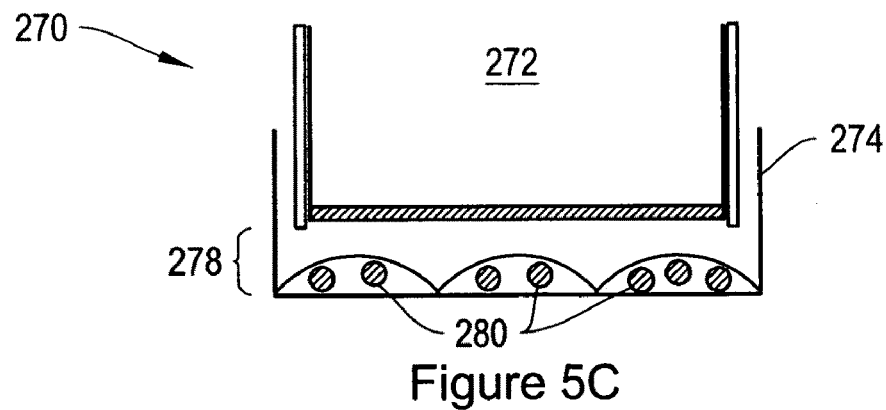

FIG. 5C illustrates a second alternative sensor arrangement 270 that includes a support 272 and a biological sample holder 274. A sensor film 276 is coupled to the distal end of the support 272. A cell monolayer 278 adheres to the surfaces of the biological sample holder 274. Alternatively, cells are suspended in a buffer. In addition, nanosensor particles 280 are introduced into the cells. In certain embodiments, the quantum dots used in the sensor film 276 differ from the quantum dots used in the nanosensor particles 280. In particular, the different quantum dots desirably have distinguishable fluorescence characteristics such that an analysis module analyzing the output of a light sensor monitoring the sensor arrangement 270 can differentiate between the output of the sensor film 272 and the nanosensor particles 280. As a result, the analysis module can differentiate between intracellular target ion concentration and extracellular target ion concentration. In an exemplary embodiment, the sensor film comprises quantum dots of a selected fluorescence wavelength, e.g., 560 nm, and the nanosensor particles comprise quantum dots of a selected fluorescence wavelength, e.g., 655 nm. In addition, the sensor film 272 may include ionophores different from those included in the sensor particles 280, e.g., nanosensor particles comprising sodium ionophores and sensor films comprising potassium ionophores. Thus, the sensor arrangement 270 can monitor the concentrations of two different target ions.

Figure 5D:
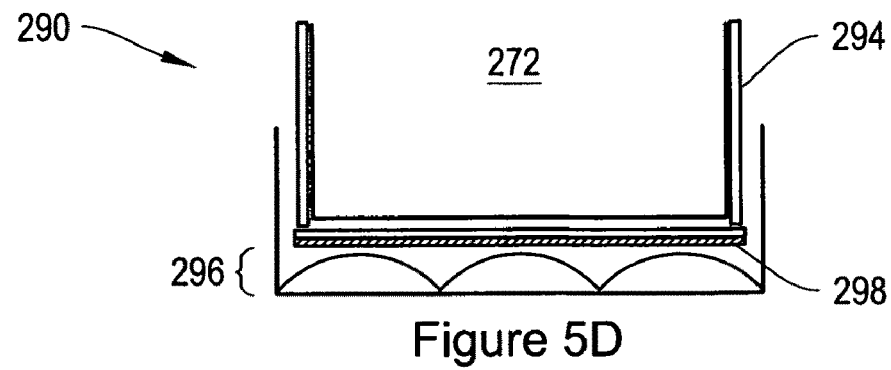

FIG. 5D illustrates a third alternative sensor arrangement 290 that includes an electrode support 292 and a biological sample holder 294. The biological sample holder 294, in addition to a cell monolayer 296 or cells suspended in a buffer, includes a removable sensor film 298. The removable sensor film 298, for example, can be a glass cover slip or other transparent surface coated with a sensor film.

In still another embodiment, the sensor film is coated onto the inner surface of the biological sample holder. And in another approach, to accommodate multiwell plates, such as the 96-well plate format often used in assays, one embodiment of the present invention utilizes round glass coverslips coated with the sensor film along with the cells to be monitored. In certain embodiments, larger multiwell plates such as 384- and 1536-well plates are applied with a layer of sensor film disposed on a surface of some or all of the wells. In these embodiments, each well contains a single sensor type to track a specific species of interest; the various sensor types may differ in the ionophore employed and utilize quantum dots with fluorescence wavelengths that are the same or similar. The compound of interest is then added directly to the well.

The multiwell plate is then placed in a fluorometer and the fluorescence intensity is monitored with time.

In a typical implementation, a plurality of biological sample holders holding biological samples is provided. Biological samples introduced into the holders may include cells suspended in a buffer solution, but alternatively cells may be adhered to the walls of the biological sample holders. Next, sensors are introduced into the biological sample holders as shown in FIGS. 5A and 5C, and/or are introduced into the cells themselves. Alternatively, the sensors can coat the walls of the biological sample holders. As described above, nanosensor particles can be introduced either by electroporating the cells via electrodes positioned in the biological sample holders or by the chemistry applied to the nanosensor particles breaching vesicle membranes within the cells. Similarly, the sensors can be introduced into the cells using pico-injection, bead loading, a gene gun, or through liposomal delivery techniques known in the art.

An agent, such as a therapeutic, toxin, biological macromolecule (such as a nucleic acid, an antibody, a protein or portion thereof, e.g., a peptide), small molecule (of 2000 amu or less, 1000 amu or less or 500 amu or less), protein, virus, bacteria, chemical compound, mixture of chemical compounds, or an extract made from biological materials such as bacteria, plants, fungi, or animal (particularly mammalian) cells or tissues, or other biologically active agent may be introduced into one or more of the biological sample holders. In one particular implementation using an array of biological sample holders, no agent is introduced into a first row of biological sample holders to preserve a control. A first agent is introduced into a second row of biological sample holders. Additional agents are added to additional rows of the array of biological sample holders. The fluorescence of the sensors introduced into the biological sample holders may be monitored. The monitoring preferably begins prior to introduction of the agents and continues thereafter. Changes in ion concentration resulting from the introduced agents are then determined. By comparing the changes in ion concentration after adding an agent, one can determine the effect of the agent on the cells being tested.

The sensors of the invention can be used to monitor the effects of pharmaceutical agents on biological systems such as the cardiovascular system or the circulatory system. Action potentials generated by cardiac or neural cells in culture are defined by a flux of sodium and potassium into and out of the cell. In certain embodiments, the sensors of the invention measure this ion flux in cardiac cells accurately and spatially in a high throughput manner.

In certain aspects, the sensors are used in the drug discovery process. In certain such embodiments, the sensors are used to measure the efficacy of a therapy. For example, ion-selective sensors may be employed to monitor the effect of ion channel-modulating drugs. In alternative embodiments, sensors are used to screen for cytotoxic substances by, for example, determining ionic flux in cardiac cells in response to a cytotoxic agent and using these values as a comparison for testing novel therapeutic agents.

In certain aspects, the sensors of the invention are implanted into small animals to monitor biological responses to new therapeutic agents. In certain embodiments, the implantable sensors are used to study the mechanism of disease in small animals. In certain such embodiments, the animals, such as rats or mice, are, for example, infected with a disease and the biological functions are monitored by detecting the signal of the implanted optical sensors. In such embodiments, the animal is placed within a monitoring element, e.g., a fluorescent monitoring cell similar to a monitoring element used to take X-rays of small animals, wherein the quantum dots of the sensors are excited, e.g., with UV light, and fluorescence emitted from the sensors within the animal may be detected.

In various embodiments the invention may be constructed to directly detect the presence of particular ions. As illustrated in the tables below, it is known in the art that certain diseases affect particular ion channels in a cell. Accordingly, assays for those ions utilizing the present invention may furnish a diagnostic tool to determine the presence of particular diseases. Accordingly, the scope of the present invention should be understood to also include the application of the heretofore-described subject matter to measure the ions set forth in the following tables, as well as their application to diagnose the presence of the associated diseases also appearing in the following tables.

| Channel | Gene | Channel-forming unit/ligand | OMIM | Disease |
|---|---|---|---|---|
| Cation channels: | | | | |
| CHRNA1/ACHRA | CHRNA1 | $\alpha$, ACh | 100690 | Myasthenia congenita |
| CHRNA4 | CHRNA4 | $\alpha$, ACh | 118504 | Autosomal dominant nocturnal frontal lobe epilepsy |
| CHRNB2 | CHRNB2 | $\beta$, ACh | 118507 | Autosomal dominant nocturnal frontal lobe epilepsy |
| Polycystin-2 | PKD2 | $\alpha$ | 173910 | Autosomal dominant polycystic kidney disease (ADPKD) |
| CNGA3 | CNGA3 | $\alpha$, cGMP | 60053 | Achromatopsia 2 (color blindness) |
| CNGB1 | CNGB1 | $\beta$, cGMP | 600724 | Autosomal recessive retinitis pigmentosa |
| CNGB3 | CNGB3 | $\beta$, cGMP | 605080 | Achromatopsia 3 |
| Sodium channels: | | | | |
| Na.1.1 | SCN1A | $\alpha$ | 182389 | Generalized epilepsy with febrile seizures (GEFS+) |
| Na.1.2 | SCN2A | $\alpha$ | 182390 | Generalized epilepsy with febrile and afebrile seizures) |
| Na.1.4 | SCN4A | $\alpha$ | 603967 | Paramyotonia congenital, potassium aggressive myotonia, hyperkalemic periodic paralysis |
| Na.1.5 | SCN5a | $\alpha$ | 600163 | Long-QT syndrome, progressive familial heart block type 1, Brugada syndrome (idiopathic ventricular arrhythmia) |
| SCN1B | SCN1B | $\beta$ | 600235 | Generalized epilepsy with febrile seizures (GEFS+) |
| ENAC$\alpha$ | SCNNIA | $\alpha$ | 600228 | Pseudohypoaldosteronism type 1 (PHA1) |
| ENaC$\beta$ | SCNN1B | $\beta$ | 600760 | PHA1, Liddle syndrome (dominant hypertension |
| ENaC$\gamma$ | SCNN1G | $\gamma$ | 600761 | PHA1, Liddle syndrome |
| Potassium channels: | | | | |

-continued

| | | | | |
|---|---|---|---|---|
| K, 1.1. | KCNA1 | α | 176260 | Episodic ataxia with myokymia |
| KCNQI/K, LQT1 | KCNQ1 | α | 192500 | Autosomal dominant long-QT syndrome (Romano-Ward) Autosomal recessive long-QT syndrome with deafness (Jervell-Lange-Nielsen) |
| KCNQ2 | KCNQ2 | α | 602235 | BFNC (epilepsy), also with myokymia |
| KCNQ3 | KCNQ3 | α | 602232 | BFNC (epilepsy) |
| KCNO4 | KCNQ4 | α | 603537 | DFNA2 (dominant hearing loss) |
| HERG/KCNH2 | KCNH2 | α | 152427 | Long-QT syndrome |
| Kir1.1/ROMK | KCNJ1 | α | 600359 | Bartter syndrome (renal salt loss, hypokalemic alkalosis) |
| Kir2.1/IRK/KCNJ2 | KCNJ2 | α | 600681 | Long-QT syndrome with dysmorphic features (Andersen syndrome) |
| Kir6.2/KATATP$_{ATP}$ | KCNJ11 | α | 600937 | Persistent hyperinsulinemic hypoglycemia of infancy (PHHI) |
| SURI | SURI | β | 600509 | PHHI |
| KCNE1/Mink/ISK | KCNE1 | β | 176261 | Autosomal dominant long-QT syndrome (Romano-Ward) Autosomal recessive long-QT syndrome with deafness (Jervell-Lange-Nielson) |
| KCNE2/MiRP1 | KCNE2 | β | 603796 | Long-QT syndrome |
| KCNE3/MiRP2 | KCNE3 | β | 604433 | Periodic paralysis |
| | | | | Calcium channels: |
| Ca, 1.1 | CACNA1S | α | 114208 | Hypokalemic periodic paralysis, malignant hyperthermia |
| Ca, 1.4 | CACNA1F | α | 300110 | X-linked congenital stationary night blindness |
| Ca, 2.1 | CACNA1A | α | 601011 | Familial hemiplegic migraine, episodic staxia, spinocerebella ataxia type 6 |
| RyRI | RYR1 | α | 180901 | Malignant hyperthermia, central core disease |
| RyR2 | RYR2 | α | 180902 | Catecholaminergic polymorphic ventricular tachycardia, arrhythmogenic right ventricular dysplasia type 2 |
| | | | | Chloride channels: |
| CFTR | ABCC7 | α | 602421 | Cystic fibrosis, congenital bilateral asplasia of vas deference |
| CIC-1 | CLCN1 | α | 118425 | Autosomal recessive (Becker) or dominant (Thomsen myotonia |
| CIC-5 | CLCN5 | α | 300008 | Dent's disease (X-linked proteinuria and kidney stones) |
| CIC-7 | CLCN7 | α | 602727 | Osteopetrosis (recessive or dominant) |
| CIC-Kb | CLCNKB | α | 602023 | Bartter syndrome type III |
| Barttin | BSND | β | 606412 | Bartter syndrome type IV (associated with sensorineural deafness) |
| GLRA1 | GLRA1 | α, glycine | 138491 | Hyperekplexin (startle desease) |
| GABAα1 | GABRA1 | α GABA | 137160 | Juvenile myoclonus epilepsy |
| GABAγ2 | GABRG2 | γ, GABA | 137164 | Epilepsy |
| | | | | Gap junction channels: |
| Cx26 | GJB2 | | 121011 | DFNB3 (autosomal dominant hearing loss) DFNB1 (autosomal recessive hearing loss) |
| Cx30 | GJB4 | | 605425 | DFNA3 |
| Cx31 | GJB3 | | 603324 | DFNA2 |
| Cx32 | GJB1 | | 304040 | CMTX (X-linked Charcot-Mari-Tooth neuropathy) |
| AChR α7 | | | | Inflammation |
| ClC7 | | | | Osteoporosis |
| Ether-a-go-go (eag, erg, elk) | | | | Cancer |
| Gardos channel | | | | Sickle cell anemia |
| P2X7 | | | | Immune disorders |
| TRPC6 | | | | Asthma, COPD |
| TRPM1 | | | | Melanoma |
| TRPM2 | | | | Asthma |
| TRPM4 | | | | Immune disorders |
| TRPM7 | | | | Stroke |
| TRPM8 | | | | Prostate cancer |
| TRPV1 | | | | Urinary incontinence, pain |

The third column classifies channel proteins into α, β, and γ subunits, where α subunits are always directly involved in pore formation, Several β subunits are only accessory (i.e., do not form pores), as is the case, for example, with SCN1B and barttin. Others (e.g. of ENaC and GABA receptors) participate in pore formation. For ligand-gated channels, the ligand is given. Note that GABA and glycine act from the extracellular side, whereas cGMP is an intracellular messenger.

| Gene | Accession ID | Gene Locus | | Tissue Expression |
|---|---|---|---|---|
| | | | Sodium Channel Type/Disease | |
| SCN1A | GDB: 118870 S71446 | 2q24 | SCN1, vg type 1, α-subunit (280 KDa) | Brain |
| SCN1B | GDB: 127281 U12188-12104 L16242, L10338 | 19q13.1 | Hs.89634, vg type 1 $\beta_1$ subunit (38 KDa) | Brain, heart, skeletal muscle |
| SCN2A1 | GDB: 120367 | 2q23 | SCN2A, HBSCI, vg type II, $\alpha_1$-subunit (280(KDa) | Brain, peripheral nerve |
| SCN2A2 | CDB: 133727 | 2q23-24.1 | HBSCH, vg type II, $\alpha_2$-subunit vg type II, $\beta_2$-subunit (33 KDa) | Brain |

| | | | | |
|---|---|---|---|---|
| SCN2B | GDB: 118871 AF019498 | | | |
| SCN3A | GDB: 132151 S69887 | 2q24-31 | vg type III, α-subunit (280 kDa) | Brain |
| SCN4A | GDB: 125181 L04216-L04236 | 17q23.1-25.3 | SkM1, vg type IV α-subunit (260 kDa), hyperkalemic periodic paralysis, paramyotonia congentia, potassturn-aggravated myotonia | Skeletal muscle |
| SCN4B | GDB: 125182 | 3q21 | vg type IV, β-subunit, | Heart, fetal skeletal muscle |
| SCN5A | GDB: 132152 | | SkM2, hH1, vg type V, α-subunit, long Q-T syndrome 3 | |
| SCN6A | GDB: 132153 | 2q21-23 | Hs99945, vg type VI, α-subunit | Heart, uterus, fetal and denervated skeletal muscle |
| | | | Calcium Channel Type/Disease | |
| SCN7A | GDB: 228137 | 12q13 | vg type VII, α-subunit | Brain, spinal cord |
| SCN8A | GDB: 631695 | | vg type VIII, α-subunit, motor end-plate disease + ataxia in mice | |
| SCN9A | GDB: 3750013 | | vg type IX, α-subunit neuroendocrine type | Thyroid and adrenal gland |
| SCN10A | GDB: 750014 | 1pter-p36.3 | hPN3, vg type X | Sensory neurons, dorsal root ganglia |
| SCNN1A | GDB: 366596 Z92978 | 12pt3 | SCNN1, nvg type 1 α-subunit of ENaC | Kidney, lung colon |
| SCNN1B | GDB: 434471 | 16p12.2-p12.1 | nvg 1 β-subunit, Liddle's syndrome pseudohypoaldosterontsm I | Kidney, lung colon |
| SCNN1D | GDB: 6053678 | 1p36.3-p36.2 | DnaCh, nvg 1 δ-subunit | Kidney, lung, colon |
| SCNN1G | GDB: 568769 X87160 | 16p122-p12.1 | nvg 1 γ-subunit, Liddle's syndrome pseudohypoaldosterontsm I | Kidney, lung, colon |
| CACNA1A CACNL1A4 | GDB: 126432 Z80114-Z80155, X99697, U79666 | 19p13 19p13.1 | P/Q type $\alpha_{1A}$-subunit, eqisodic ataxia 2, familial hemiplegic migraine, spinocerebellar ataxia 6; tottering, leaner, and rolling mice | Brain (cortex, bulbus, olfacorius, hippocarnpus, cerebellum, brain stem), motoneurons, kidney |
| CACNA1B CACNL1A5 | GDB: 580689 M94172, M94173 | 9q34 | CACNN, N-type $\alpha_{1A}$-subunit | Central, peripheral nervous system |
| CACNA1C CACNL1A1 | GDB: 126094 L29636, L29634, L29629 | 12p13 12p13.3 | CCHL1A1, L-type $\alpha_{1A}$-subunit | Heart, fibroblasts, lung, smooth muscle (2 splice variants) |
| CACNA1D CACNL1A2 | GDB: 128872 | 3p14.3 3p21.3.2? | CCHL1A2, L-type $\alpha_{1D}$-subunit | Brain, pancreas, neuroendocrine |
| CACNA1E CACNL1A6 | GDB: 434408 | 1q25-31 | R-type $\alpha_{1C}$-subunit | Brain, skeletal muscle (end plate) |
| CACNA1F | GDB: 6053864 | Xp11.23-11.22 | $\alpha_{1F}$-Subunit | Retina |
| GACNIAG | AF27964 | 17q22 | T-type $\alpha_{1G}$-subunit | Brain |
| CACNA1S CACNL1A8 | GDB: 126431 Z22672, L33798 U30666-U30707 | 1q31-32 | L-type $\alpha_{1B}$-subunit (5% 212, 95% 190 kDa), malignant hyperthermia 5, hypokalernic periodic paralysis | Skeletal muscle (brain, kidney) |
| CACNA2 CACNL2A | GDB: 132010 Z28613, Z28609 Z28605, Z28602 Z28699, M76559 | 7q21-22 | CACNA2, CACNA2D1, $\alpha_8$-subunit (175 kDa), MHS3 | $\alpha_{2A}$; skeletal muscle, heart, brain, ileum; $\alpha_{2B}$; brain; $\alpha_{2CVD}$; aorta |
| CACNB1 CACNLB1 | GDB: 132012 GDB: 1073281 U86952-U86961 M76560, L06111 GDB: 193328 | 17q21-22 | $\beta_1$-Subunit (524 aa, 54 kDa) | $\beta_1$A/M; skeletal muscle $\beta_1$B/C; brain, heart, spleen |
| CACNB2 CACNLB2 | GDB: 132014 Q08289 | 10p12 | MYSB, $\beta_2$-subunit | $\beta_2$A/B/E; brain, heart, lung, aorta |
| CACNB3 CACNLB3 | GDB: 341023 L27584 | 12q13 | $\beta_2$-subunit (482 aa) | Brain, heart, lung, spleen, skeletal and smooth muscle, aorta, trachea, ovary, colon |
| CACNB4 | GDB: 6028693 | 2q22-23 | $\beta_2$-subunit, lethargic mice | Brain, kidney |
| CACNG CACNLG | GDB: 132015 L07738 | 17q24 | γ-Subunit (222 aa, 30 kDa) | Skeletal muscle, lung |
| CACNG2 | | | γ2-Subunit, stargazin, absence epilepsy stargazer, waggler mice | Brain |
| RYR1 | GDB: 120359 | 19q13.1 | Ryanodine receptor 1, Ca release channel, 3 splice variants, malignant hyperthermia 1, central core disease | Skeletal muscle, testis, brain, submaxillary and adrenal glands, spleen |
| RYR2 | GDB: 125278 | 1pter-qter 1q42.1-43 | RYR2, calcium release channel | Heart, smooth muscle |
| RYR3 | GDB: 138451 | 15q14 15q14-15 | RYR3, calcium release channel | Brain, neonatal skeletal muscle, adult diaphragm |

-continued

| | | | Potassium Channel Type/Disease | |
|---|---|---|---|---|
| KCNA1 | GDB: 127903 LO2750 | 12p13 | RBK1, HUK1, MBK1, AEMK, Kv1.1, Shaker homolog 1, Shaker, episodic ataxia 1 (with myokymia) | Brain, nerve, heart, skeletal muscle, retina, pancreatic islet |
| KCNA1B | | 3q26.1 | Kvβ1.1, Kvβ1.3 (splice product), β-subunit | |
| KCNA2 | GDB: 128062 X17622 | 12pter-qter | HK4, Kv1.2, Shaker homolog 2 | Brain, nerve, heart, pancreatic islet |
| KCNA2B | | 1p36.3 | Kvβ1.2, β-subunit | |
| KCNA8 | GDB: 128079 L23499 | 1p13.3 | Hs.1750, MK3, HLK3, HPCN3, Kv1.3, Shaker homolog 3 | Skeletal muscle, lymphocytes (brain, lung, thymus, spleen) |
| KCNA4 | GDB: 126730 M60450 M55514 | 11p14 | Hs.89647, Hs.1854, HK1, HPCN2, Kv1.4, Shaker homolog 4 | Brain, nerve, heart, fetal skeletal muscle, pancreatic islet |
| KCNA4L | GDB: 386059 | 11q14 | Shaker homolog type 4-like | |
| KCNA5 | GDB: 127904 M83254 M60451 | 12p13.3-13.2 12p13 12p13.33-12.31 | Hs.89509, HK2, HPCNI, Kv1.5 Shaker homolog 5 | Brain, heart, kidney, lung, skeletal muscle, pancreatic islet |
| KCNA6 | GDB: 128080 X17622 | 12p13 | HBK2, Kv1.6, Shaker homolog 6 | Brain, pancreatic islet |
| KCNA7 | GDB: 127905 | 19q13.3 | HAK6, Kv1.7 Shaker homolog 7 | |
| KCNA8 | | | see KCNQ1 | |
| KCNA9 | | | see KCNQ1 | |
| KCNA10 | GDB: 5885822 | | Shaker homolog type 10, cGMP activated | |
| KCNB1 | GDB: 128081 | 20q13.2 | Kv2.1, Shab homolog 1 | Brain, heart, kidney, retina, skeletal muscle |
| KCNB2 | | | Kv2.2, Shab homolog 2 | Brain, heart, retina |
| KCNC1 | GDB: 128082 S56770 M96747 | 11p15.1 | Kv3.1, Shaw homolog 1 | Brain, skeletal muscle, spleen, lymphocytes |
| KCNC2 | GDB: 127906 | 19q13.3-13.4 | Kv3.2, Shaw homolog 2 | Brain |
| KCNC3 | GDB: 127907 | 19q13.3 | Kv3.3, Shaw homolog 3 | Brain, liver |
| KCNC4 | GDB: 127908 | 1p21 | Kv3.4, HKSHIIIC, Shaw homolog 4 | Brain, skeletal muscle |
| KCND1 | GDB: 128083 | | Kv4.1, Shal hormolog 1 | Brain |
| KCND2 | GDB: 134771 | | RK5, Kv4.2, Shal homolog 2 | Brain, heart, aorta |
| KCND3 | GDB: 134772 | | Kv4.3, KSHIVB, Shal homolog 3 | |
| KCNE1 | GDB: 127909 | 21q22.1-22.2 | MinK, ISK, vg Isk homolog 1 (129 aa), long Q-T syndrome 5 | Kidney, submandibular gland, uterus, heart, cochlea, retina |
| KCNMA1 | GDB: 386031 U09383-4 U02632 | 10pter-qter 7q32.1 | SLO, Hs.62679, α-subunit member 1, α-subunit of maxiK or BK channel | Fetal skeletal muscle |
| KCNMB1 | GDB: 6099615 U42600 | 5q34 | hSLO-β, β-subunit member 1 (191 aa), β-subunit of max1K or BK channel | Smooth, fetal skeletal muscle, brain (hippocampus, corpus callosum) |
| KCNN1 | U69883 | | SK(Ca)1, small-conductance Ca-activated K channel, apamin-insensitive | Brain, heart |
| KCNN2 | | | SK(Ca)2, apamin sensitive | Brain, adrenal gland |
| KCNN3 | Y08263 AA285078 | 1q? | SK(Ca)3, small-conductance Ca-activated K channel, intermediate apamin sensitivity | Brain, heart, (human embryonic) skeletal muscle, liver |
| KCNN4 | AF022150 AF022797 AF033021 AF000972 | 19q13.2 | IK1, intermediate-conductance Ca-activated K channel, KCa4, SK4, Gantos channel | T lymphocytes, colon, smooth muscles, prostata, red blood cells, neurons |
| KCNQ1 | GDB: 741244 U40990 | 11p15.5 | KCNA9, (KV)LQT1, KQT-like subfamily member 1, long Q-T syndrome 1 | Heart, cochlea, kidney, lung, placenta, colon |
| KCNQ2 | GDB: 9787229, Y15065, AF033348 | 20q13.3 | KQT-like subfamily member 2 (872 aa) | Brain |
| KCNQ3 | GDB: 9787230 AF033347 | 8q24.22-24.3 | KQT-like subfamily member 3 (825 aa) | Brain |
| HERG | GDB: 407638 | 7q35-36 | HERG, similar to ether-a-go go (eag), Ikr, long Q-T syndrome 2 | Brain, heart |
| KCNJ1 | GDB: 204206 U65406, U12541 | 11q24 | ROMK1, Kirl.1, Hs.463, Bartter/hyperprostaglandin E syndrome | Kidney, pancreatic islets |
| KCNJ2 | GDB: 278964 U12507 | 17pter-qter | IRK1, Kir2.1, Hs.1547 | Muscle, neural tissue, heart |
| KCNJ3 | GDB: 278325 U50964 | 2q24.1 | GIRK1, Kir3.1 | Heart, cerebellum |
| KCNJ4 | GDB: 374080 Z97056 | 22q13.1 | HIR, HIRK1, HIRK2, Kir2.3 | Heart, skeletal muscle, brain |
| KCNJ5 | GDB: 547948 | 11q24 | CIR, KATP1, GIRK4, Kir3.4 | Heart, pancreas |

-continued

| | | | | |
|---|---|---|---|---|
| KCNJ6 | GDB: 547949 U24660 | 21q22.1 | KCNJ7, GIRK2, KATP2, BIR1, Kir3.2, ataxia, weaver mice | Cerebellum, pancreatic islet |
| KCNJ8 | GDB: 633096 | 12p11.23] | Kir6.1, uKATP, ubiquitious $K_{ATP}$ α-subunit | Brain, heart, skeletal, smooth muscle, others |
| KCNJ10 | GDB: 3750203 | 1q22-23 | Kir1.2, Kir4.1 | Glia |
| KCNJ11 | GDB: 7009893 | [11p15.1] | Kir6.2, BIR, K(ATP) α-subunit, hyperinsulinemic hypoglycemia | Pancreatic islets |
| KCNJ12 | GDB: 4583927 | [17p11.1] | Kir2.2 | |
| KCNJ15 | GDB: 6275865 | [21q22.2] | Kir4.2 | |
| KCNJN1 | GDB: 6108062 | [ ] | Kir2.2v, subfamily inhibitor 1 | |
| SUR1 | GDB: 591970 | [11p15.1] | SUR(1), sulfonylurea receptor, K(ATP) β-subunit, hyperinsulinemic hypoglycemia | Pancreatic islets |
| SUR2 | | 12p12.1] | SUR2, SUR2A, B, sulfonylurea receptor 2 (1545-aa), β-subunit of K(ATP) | 2A: heart, 2B: brain, liver, skeletal, smooth muscle, urinary bladder |
| KCNK1 | GDB: 6045446 | 1q42-43 | DPK, TWIK1 | Kidney |
| KCNK2 | | 1q41 | TREK1 | Brain |
| KCNK3 | GDB: 9773281 | 2p23 | TASK | Kidney |

| Therapeutic Target | Enzyme Family | Assay |
|---|---|---|
| Alzheimer's | CMGC | ERK2 (P42mapk) |
| Alzheimer's | Phospholipase | PLA2 |
| Alzheimer's | Cyclooxygenases | COX2 |
| Alzheimer's | CaMK | MARKI |
| Alzheimer's | CaMK | MARK2 |
| Alzheimer's | AGC | PKCalpha |
| Alzheimer's | AGC | PKCgamma |
| Alzheimer's | AGC | PKCgamma |
| Alzheimer's | Cysteine proteases | caspase-3 |
| Alzheimer's | Cysteine proteases | caspase-6 |
| Alzheimer's | Aspartic proteases | BACE-1 (beta-secretase) |
| Alzheimer's | Aspartic proteases | cathepsin D |
| Alzheimer's | Aspartic proteases | cathepsin E |
| Alzheimer's | Metalloproteases | ACE |
| Alzheimer's | Metalloproteases | ACE |
| Alzheimer's | Metalloproteases | TACE |
| Alzheimer's | NO synthases | constitutive NOS (cerebellar) |
| Alzheimer's | Monoamine &neurotransmitter synthesis & metabolism | acetylcholinesterase |
| Alzheimer's | Monoamine &neurotransmitter synthesis & metabolism | COMT (catechol-O-methyl transferase) |
| Alzheimer's | Monoamine &neurotransmitter synthesis & metabolism | MAO-A |
| Alzheimer's | Monoamine &neurotransmitter synthesis & metabolism | MAO-B |
| Alzheimer's | Monoamine &neurotransmitter synthesis & metabolism | tyrosine hydroxylase |
| Alzheimer's | Phospholipase C | PLC |
| Alzheimer's | Miscellaneous enzymes | xanthine oxidase/ superoxide 02-scavenging |
| Dependence/Addiction | AGC | PKA |
| Dependence/Addiction | AGC | PKCalpha |
| Dependence/Addiction | AGC | PKCbeta 1 |
| Dependence/Addiction | AGC | PKCbeta 2 |
| Dependence/Addiction | AGC | PKCdelta |
| Dependence/Addiction | Monoamine &neurotransmitter synthesis & metabolism | GABA transaminase |
| Dependence/Addiction | Cyclases | adenylyl cyclase (stimulated) |
| Dependence/Addiction | Phospholipase C | PLC |
| Dependence/Addiction | ATPase | ATPase ($Na^+/K^+$) |
| Inflammation/Arthritis/Allergy | RTK | EGFR kinase |
| Inflammation/Arthritis/Allergy | RTK | FLT-1 kinase (VEGFR1) |
| Inflammation/Arthritis/Allergy | RTK | KDR kinase (VEGFR2) |
| Inflammation/Arthritis/Allergy | CTK | Fyn kinase |
| Inflammation/Arthritis/Allergy | CTK | HCK |

-continued

| Therapeutic Target | Enzyme Family | Assay |
|---|---|---|
| Inflammation/Arthritis/Allergy | CTK | Lek kinase |
| Inflammation/Arthritis/Allergy | CTK | Lyn kinase |
| Inflammation/Arthritis/Allergy | CTK | ZAP70 kinase |
| Inflammation/Arthritis/Allergy | CMGC | ERK2 (P42mapk) |
| Inflammation/Arthritis/Allergy | CMGC | JNK 1 |
| Inflammation/Arthritis/Allergy | CMGC | JNK 2 |
| Inflammation/Arthritis/Allergy | CMGC | P38alpha kinase |
| Inflammation/Arthritis/Allergy | Phospholipase | PLA2 |
| Inflammation/Arthritis/Allergy | Cyclooxygenases | COX1 |
| Inflammation/Arthritis/Allergy | Cyclooxygenases | COX2 |
| Inflammation/Arthritis/Allergy | TXA2 synthetase | TXA2 synthetase |
| Inflammation/Arthritis/Allergy | CaMK | MAPKAPK2 |
| Inflammation/Arthritis/Allergy | AGC | PKA |
| Inflammation/Arthritis/Allergy | Lipoxygenases | 12-lipoxygenase |
| Inflammation/Arthritis/Allergy | Lipoxygenases | 15-lipoxygenase |
| Inflammation/Arthritis/Allergy | Serine proteases | elastase |
| Inflammation/Arthritis/Allergy | Serine proteases | cathepsin G |
| Inflammation/Arthritis/Allergy | Serine proteases | kallikrein |
| Inflammation/Arthritis/Allergy | Serine proteases | tryptase |
| Inflammation/Arthritis/Allergy | Cysteine proteases | caspase-1 |
| Inflammation/Arthritis/Allergy | Cysteine proteases | caspase-4 |
| Inflammation/Arthritis/Allergy | Cysteine proteases | caspase-5 |
| Inflammation/Arthritis/Allergy | Cysteine proteases | cathepsin B |
| Inflammation/Arthritis/Allergy | Cysteine proteases | cathepsin X |
| Inflammation/Arthritis/Allergy | Aspartic proteases | cathepsin E |
| Inflammation/Arthritis/Allergy | Metalloproteases | MMP-1 |
| Inflammation/Arthritis/Allergy | Metalloproteases | MMP-2 |
| Inflammation/Arthritis/Allergy | Metalloproteases | MMP-3 |
| Inflammation/Arthritis/Allergy | Metalloproteases | MMP-7 |
| Inflammation/Arthritis/Allergy | Metalloproteases | MMP-8 |
| Inflammation/Arthritis/Allergy | Metalloproteases | MMP-9 |
| Inflammation/Arthritis/Allergy | Metalloproteases | MMP-13 |
| Inflammation/Arthritis/Allergy | Metalloproteases | MT1-MMP (MMP-14) |
| Inflammation/Arthritis/Allergy | Metalloproteases | TACE |
| Inflammation/Arthritis/Allergy | Phosphatases | phosphatase CD45 |
| Inflammation/Arthritis/Allergy | Phosphodiesterases | PDE2 |
| Inflammation/Arthritis/Allergy | Phosphodiesterases | PDE4 |
| Inflammation/Arthritis/Allergy | Phosphodiesterases | acid sphingomyelinase |
| Inflammation/Arthritis/Allergy | Monoamine & neurotransmitter synthesis & metabolism | HNMT (histamine N-methyltransferase) |
| Inflammation/Arthritis/Allergy | Miscellaneous enzymes | myeloperoxidase |
| Inflammation/Arthritis/Allergy | Miscellaneous enzymes | xanthine oxidase/ superoxide 02-scavenging |
| Neuroprotection | RTK | TRKB |
| Neuroprotection | CMGC | CDK5 |
| Neuroprotection | CMGC | DYRK1a |
| Neuroprotection | CMGC | ERK1 |
| Neuroprotection | CMGC | ERK2 (P42mapk) |
| Neuroprotection | MCGC | JCK 3 |

-continued

| Therapeutic Target | Enzyme Family | Assay |
|---|---|---|
| Inflammation/Arthritis/Allergy | Metalloproteases | MMP-13 |
| Inflammation/Arthritis/Allergy | Metalloproteases | MT1-MMP (MMP-14) |
| Inflammation/Arthritis/Allergy | Metalloproteases | TACE |
| Inflammation/Arthritis/Allergy | Phosphatases | phosphatase CD45 |
| Inflammation/Arthritis/Allergy | Phosphodiesterases | PDE2 |
| Inflammation/Arthritis/Allergy | Phosphodiesterases | PDE4 |
| Inflammation/Arthritis/Allergy | Phosphodiesterases | acid sphingomyelinase |
| Inflammation/Arthritis/Allergy | Monoamine & neurotransmitter synthesis & metabolism | HNMT (histamine N-methyltransferase) |
| Inflammation/Arthritis/Allergy | Miscellaneous enzymes | myeloperoxidase |
| Inflammation/Arthritis/Allergy | Miscellaneous enzymes | xanthine oxidase/superoxide 02-scavenging |
| Neuroprotection | RTK | TRKB |
| Neuroprotection | CMGC | CDK5 |
| Neuroprotection | CMGC | DYRK1a |
| Neuroprotection | CMGC | ERK1 |
| Neuroprotection | CMGC | ERK2 (P42mapk) |
| Neuroprotection | MCGC | JCK 3 |
| Neuroprotection | Cyclooxygenases | COX1 |
| Neuroprotection | Cyclooxygenases | COX2 |
| Neuroprotection | CaMK | CaMK2alpha |
| Neuroprotection | AGC | PKA |
| Neuroprotection | Cysteine proteases | caspase-3 |
| Neuroprotection | Phosphodiesterases | PDE1 |
| Neuroprotection | Phosphodiesterases | PDE6 |
| Neuroprotection | NO synthases | constitutive NOS (endothelial) |
| Neuroprotection | NO synthases | constitutive NOS (cerebellar) |
| Neuroprotection | Monoamine & neurotransmitter syntheses & metabolism | acetylcholinesterase |
| Neuroprotection | Monoamine & neurotransmitter syntheses & metabolism | COMT (catechol-O-methyl transferase) |
| Neuroprotection | Monoamine & neurotransmitter syntheses & metabolism | GABA transaminase |
| Neuroprotection | Monoamine & neurotransmitter syntheses & metabolism | HNMT (histamine N-methyltransferase) |
| Neuroprotection | Monoamine & neurotransmitter syntheses & metabolism | MAO-A |
| Neuroprotection | Monoamine & neurotransmitter syntheses & metabolism | MAO-A |
| Neuroprotection | Monoamine & neurotransmitter syntheses & metabolism | PNMT (phenylethanoiamine-N-methyl transferase) |
| Neuroprotection | Monoamine & neurotransmitter syntheses & metabolism | tyrosine hydroxylase |
| Neuroprotection | Cyclases | guanylyl cyclase (basal) |
| Neuroprotection | Cyclases | guanylyl cyclase (stimulated) |
| Neuroprotection | ATPase | ATPase (Na+/K+) |
| Neuroprotection | Miscellaneous enzymes | xanthine oxidase/superoxide 02-scavenging |
| Parkinson | CMGC | JNK 1 |
| Parkinson | Phospholipase | PLA2 |
| Parkinson | Cyclooxygenases | COX2 |
| Parkinson | Cysteine proteases | caspase-3 |
| Parkinson | NO synthases | constitutive NOS (cerebellar) |

-continued

| Therapeutic Target | Enzyme Family | Assay |
|---|---|---|
| Parkinson | Monoamine & neurotransmitter syntheses & metabolism | acetylcholinesterase |
| Parkinson | Monoamine & neurotransmitter syntheses & metabolism | COMT (catechol-O-methyl transferase |
| Parkinson | Monoamine & neurotransmitter syntheses & metabolism | MAO-A |
| Parkinson | Monoamine & neurotransmitter syntheses & metabolism | MAO-B |
| Cancer | RTK | Axl kinase |
| Cancer | RTK | c-kit kinase |
| Cancer | RTK | c-kit kinase |
| Cancer | RTK | EGFR kinase |
| Cancer | RTK | EphA1 kinase |
| Cancer | RTK | EphA3 kinase |
| Cancer | RTK | EphA4 kinase |
| Cancer | RTK | EphB2 kinase |
| Cancer | RTK | FGFR1 kinase |
| Cancer | RTK | FGFR2 kinase |
| Cancer | RTK | FGFR3 kinase |
| Cancer | RTK | FGFR4 kinase |
| Cancer | RTK | FLT-1 kinase (VEGFR1) |
| Cancer | RTK | FLT-3 kinase |
| Cancer | RTK | FLT-4 kinase (VEGFR3) |
| Cancer | RTK | Fms/CSFR kinase |
| Cancer | RTK | HER2/ErbB2 kinase |
| Cancer | RTK | HER4/ErbB4 kinase |
| Cancer | RTK | KDR kinase (VEGFR2) |
| Cancer | RTK | PDGFRalpha kinase |
| Cancer | RTK | PDGFRbeta kinase |
| Cancer | RTK | Ret kinase |
| Cancer | RTK | TIE2 kinase |
| Cancer | RTK | TRKA |
| Cancer | CTK | Abl kinase |
| Cancer | CTK | BLK |
| Cancer | CTK | BMX (Bk) kinase |
| Cancer | CTK | BRK |
| Cancer | CTK | BTK |
| Cancer | CTK | CSK |
| Cancer | CTK | FAK |
| Cancer | CTK | Fes kinase |
| Cancer | CTK | Fyn kinase |
| Cancer | CTK | JAK2 |
| Cancer | CTK | JAK3 |
| Cancer | CTK | Lck kinase |
| Cancer | CTK | PYK2 |
| Cancer | CTK | Src kinase |
| Cancer | CTK | Syk |
| Cancer | CTK | Yes kinase |
| Cancer | CMGC | CDC2/CDK1 (cycB) |
| Cancer | CMGC | CDK2 (cycE) |
| Cancer | CMGC | CDK4 (cycD1) |
| Cancer | CMGC | CDK5 |
| Cancer | CMGC | CK2 (casein kinase 2) |
| Cancer | CMGC | DYRK1a |
| Cancer | CMGC | ERK1 |
| Cancer | CMGC | ERK2 (P42mapk) |
| Cancer | CMGC | HIPK2 |
| Cancer | CMGC | IKKalpha |
| Cancer | CMGC | IKKbeta |
| Cancer | CMGC | JNK 1 |
| Cancer | CMGC | JNK 2 |
| Cancer | CMGC | NEK1 |
| Cancer | CMGC | NEK2 |
| Cancer | CMGC | NEK4 |
| Cancer | CMGC | p38alpha kinase |
| Cancer | CMGC | p38beta 2 kinase (SAPK2b2) |
| Cancer | CMGC | p38delta kinase |
| Cancer | CMGC | p38gamma kinase |
| Cancer | Cyclooxygenases | COX2 |
| Cancer | CaMK | CaMKldelta |
| Cancer | CaMK | CaMK |
| Cancer | CaMK | CHK1 |
| Cancer | CaMK | CHK2 |

| Therapeutic Target | Enzyme Family | Assay |
| --- | --- | --- |
| Cancer | CaMK | DAPK1 |
| Cancer | CaMK | DAPK2 |
| Cancer | CaMK | MAPKAPK2 |
| Cancer | CaMK | MAPKAPK3 |
| Cancer | CaMK | MAPKAPK5 (PRAKO |
| Cancer | CaMK | MAARK1 |
| Cancer | CaMK | MARK2 |
| Cancer | CaMK | MARK4 |
| Cancer | CaMK | Pim 1 kinase |
| Cancer | CaMK | Pirn2 kinase |
| Cancer | AGC | Aktl/PKBalpha |
| Cancer | AGC | Akt2/PKBbeta |
| Cancer | AGC | Akt3/PKBgamma |
| Cancer | AGC | AurA/Aur2 kinase |

| Therapeutic Target | Enzyme Family | Assay |
| --- | --- | --- |
| Cancer | AGC | AurB/Aurl kinase |
| Cancer | AGC | AurC/Aur3 kinase |
| Cancer | AGC | P70S6Ke |
| Cancer | AGC | PDK1 |
| Cancer | AGC | PKA |
| Cancer | AGC | PKCalpha |
| Cancer | AGC | PKCbeta 1 |
| Cancer | AGC | PKCbeta 2 |
| Cancer | AGC | PKCdelta |
| Cancer | AGC | PKCgamma |
| Cancer | AGC | PKG2 |
| Cancer | AGC | ROCK1 |
| Cancer | AGC | ROCK2 |
| Cancer | AGC | RSK2 |
| Cancer | AGC | SGKI |
| Cancer. | Lipoxygenases | 12-lipoxygenase |
| Cancer | TKL | RAF-1 kinase |
| Cancer | STE | MEK1/MAP2KI |
| Cancer | STE | MKK4/JNK1 |
| Cancer | STE | MKK6 |
| Cancer | STE | PAK1 |
| Cancer | STE | PAK2 |
| Cancer | Serine proteases | elastase |
| Cancer | Serine proteases | cathepsin G |
| Cancer | Cysteine proteases | caspase-2 |
| Cancer | Cysteine proteases | caspase-3 |
| Cancer | Cysteine proteases | caspase-8 |
| Cancer | Cysteine proteases | caspase-9 |
| Cancer | Cysteine proteases | cathepin B |
| Cancer | Cysteine proteases | cathepsin H |
| Cancer | Cysteine proteases | cathepsin L |
| Cancer | Cysteine proteases | cathepsin X |
| Cancer | Aspartic proteases | cathepsin D |
| Cancer | Aspartic proteases | cathepsin E |
| Cancer | Metalloproteases | MMP-1 |
| Cancer | Metalloproteases | MMP-2 |
| Cancer | Metalloproteases | MMP-3 |
| Cancer | Metalloproteases | MMP-7 |
| Cancer | Metalloproteases | MMP-8 |
| Cancer | Metalloproteases | MMP-9 |
| Cancer | Metalloproteases | MMP-12 |
| Cancer | Metalloproteases | MMP-13 |
| Cancer | Metalloproteases | MT1-MMP (MMP-14) |
| Cancer | Metalloproteases | TACE |
| Cancer' | Metalloproteases | MMP-1 |
| Cancer | Phosphatases | Phosphatase 1B |
| Cancer | Phosphatases | Phosphatase 2B |
| Cancer | Phosphodiesterases | PDE2 |
| Cancer | Phosphodiesterases | PDE4 |
| Cancer | Phosphodiesterases | PDES |
| Cancer | Phosphodiesterases | acid spingomyelinase |
| Cancer | NO synthases | constitutive NOS (endothelial) |
| Cancer | NO synthases | constitutive NOS (cerebellar) |
| Cancer | Cyclases | adenylyl cyclase (basal) |
| Cancer | Cyclases | adenylyl cyclase (stimulated) |
| Cancer | Phospholipase C | PLC |
| Cancer | Miscellaneous enzymes | myeloperoxidase |
| Cancer | Miscellaneous enzymes | xanthine oxidase/superoxide 02-scavenging |
| Diabetes | RTK | Ax1 kinase |
| Diabetes | RTK | EGFR kinase |
| Diabetes | RTK | IGFIR kinase |
| Diabetes | CMGC | ERK2 (P42mapk) |
| Diabetes | CMGC | Jnk1 |
| Diabetes | Cyclooxygenases | COX2 |
| Diabetes | TXA2 synthetase | TXA2 synthetase |
| Diabetes | CaMK | AMPKalpha |
| Diabetes | AGC | Aktl/PKBalpha |
| Diabetes | AGC | Akt2/PKBbeta |
| Diabetes | AGC | Akt3/PKBgamma |
| Diabetes | AGC | PDK1 |
| Diabetes | AGC | PKA |
| Diabetes | AGC | PKCalpha |
| Diabetes | AGC | PKCbeta I |
| Diabetes | AGC | PKCbeta 2 |
| Diabetes | AGC | PKCgamma |
| Diabetes | AGC | SGK2 |
| Diabetes | Metalloproteases | ACE |
| Diabetes | Metalloproteases | MMP-1 |
| Diabetes | Metalloproteases | MMP-2 |
| Diabetes | Metalloproteases | MMP-3 |
| Diabetes | Metalloproteases | MMP-7 |
| Diabetes | Metalloproteases | MMP-8 |
| Diabetes | Metalloproteases | MMP-9 |
| Diabetes | Metalloproteases | MT1-MMP (MMP-14) |
| Diabetes | Metalloproteases | TACE |
| Diabetes | Phosphodiesterases | PDE3 |
| Diabetes | Phosphodiesterases | PDE4 |
| Diabetes | Phosphodiesterases | PDE5 |
| Diabetes | NO synthases | constitutive NOS (endothelial) |
| Diabetes | Monoamine & neurotransmitter synthesis & metabolism | acetylcholinesterase |
| Diabetes | Monoamine & neurotransmitter synthesis & metabolism | GABA transaminase |
| Diabetes | Monoamine & neurotransmitter synthesis & metabolism | MAO-B |
| Diabetes | Cyclases | adenylyl cyclase (basal) |
| Diabetes | Miscellaneous enzymes | acetylCoA synthetase |
| Diabetes | Miscellaneous enzymes | HMG-CoA reductase |
| Diabetes | Miscellaneous enzymes | xanthine oxidase/superoxide 02-scavenging |
| Metabolic Diseases | Cyclooxygenases | COX2 |
| Metabolic Diseases | AGC | PICA |

-continued

| Therapeutic Target | Enzyme Family | Assay |
|---|---|---|
| Metabolic Diseases | Metalloproteases | ACE |
| Metabolic Diseases | Phosphodiesterases | PDE3 |
| Metabolic Diseases | Phosphodiesterases | PDE4 |
| Metabolic Diseases | NO synthases | constitutive NOS (endothelial) |
| Metabolic Diseases | Miscellaneous enzymes | acetylCoA synthetase |
| Metabolic Diseases | Miscellaneous enzymes | HMG-CoA reductase |
| Metabolic Diseases | Miscellaneous enzymes | xanthine oxidase/superoxide 02-scavenging |
| Obesity | CTK | PYK2 |
| Obesity | CMGC | JNK1 |
| Obesity | CaMK | AMPJakoga |
| Obesity | AGC | PKA |
| Obesity | Metalloproteases | ACE |
| Obesity | Metalloproteases | ACE |
| Obesity | Phosphatases | phosphatase IB |
| Obesity | Phosphodiesterases | PDE2 |
| Obesity | Phosphodiesterases | PDE3 |
| Obesity | Monoamine & neurotransmitter synthesis & metabolism | acetylcholinesterase |
| Obesity | ATPase | ATPase (Na+/K+) |
| Obesity | Miscellaneous enzymes | HMG-CoA reductase |
| Reproduction | Phospholipase | PLA2 |
| Reproduction | Cyclooxygenases | COX1 |
| Reproduction | Cyclooxygenases | COX2 |
| Reproduction | Phosphodiesterases | PDE5 |
| Reproduction | NO synthases | constitutive NOS (endothelial) |
| Reproduction | Cyclases | guanylyl cyclase (stimulated) |
| Cystic Fibrosis | Phospholipase | PLA2 |
| Cystic Fibrosis | TXA2 synthetase | TXA2 synthetase |
| Cystic Fibrosis | AGC | PKA |
| Cystic Fibrosis | AGC | PKCbeta 1 |
| Cystic Fibrosis | AGC | PKCbeta 2 |
| Cystic Fibrosis | Serine proteases | elastase |
| Cystic Fibrosis | Serine proteases | cathepsin G |
| Cystic Fibrosis | Metalloproteases | MMP-2 |
| Cystic Fibrosis | Phosphodiesterases | PDE3 |
| Cystic Fibrosis | Phosphodiesterases | PDE5 |
| Cystic Fibrosis | Cyclases | adenylyl cyclase (stimulated) |
| Cystic Fibrosis | Phospholipase C | PLC |
| Cystic Fibrosis | Miscellaneous enzymes | myeloperoxidase |
| Immunosuppression Profile | RTK | EGFR kinase |
| Immunosuppression Profile | CTK | JAK3 |
| Immunosuppression Profile | CMGC | ERK2 (P42mapk) |
| Immunosuppression Profile | Cyclooxygenases | COX1 |
| Immunosuppression Profile | Cyclooxygenases | COX2 |
| Immunosuppression Profile | Serine proteases | elastase |
| Immunosuppression Profile | Serine proteases | cathepsin G |
| Immunosuppression Profile | Serine proteases | tryptase |
| Immunosuppression Profile | Cysteine proteases | cathepsin B |
| Immunosuppression Profile | Metalloproteases | ECE-1 |
| Immunosuppression Profile | Metalloproteases | ECE-1 |
| Immunosuppression Profile | Metalloproteases | MMP-1 |
| Immunosuppression Profile | Metalloproteases | MMP-2 |
| Immunosuppression Profile | Metalloproteases | MMP-9 |
| Immunosuppression Profile | Phosphatases | phosphatase CD45 |
| Immunosuppression Profile | Phosphodiesterases | PDE4 |
| Immunosuppression Profile | Phosphodiesterases | acid spingomyelinase |
| Immunosuppression Profile | Cyclases | adenylyl cyclase (basal) |
| Immunosuppression Profile | Cyclases | adenylyl cyclase (stimulated) |
| Migraine | Cyclooxygenases | COX2 |
| Migraine | NO synthases | constitutive NOS (cerebellar) |
| Migraine | Monoamine & neurotransmitter synthesis & metabolism | GABA transaminase |
| Migraine | Cyclases | guanylyl cyclase (stimulated) |
| Pain | CMGC | ERK2 (42mapk) |
| Pain | Phospholipase | PLA2 |
| Pain | Cyclooxygenases | COXI |
| Pain | Cyclooxygenases | COX2 |
| Pain | AGC | PICA |
| Pain | Serine proteases | elastase |
| Pain | Metalloproteases | MMP-1 |
| Pain | Metalloproteases | MMP-2 |
| Immunosuppression Profile | Serine proteases | elastase |
| Immunosuppression Profile | Serine proteases | cathepsin G |
| Immunosuppression Profile | Serine proteases | tryptase |
| Immunosuppression Profile | Cysteine proteases | cathepsin B |
| Immunosuppression Profile | Metalloproteases | ECE-1 |
| Immunosuppression Profile | Metalloproteases | ECE-1 |
| Immunosuppression Profile | Metalloproteases | MMP-1 |
| Immunosuppression Profile | Metalloproteases | MMP-2 |
| Immunosuppression Profile | Metalloproteases | MMP-9 |
| Immunosuppression Profile | Phosphatases | Phosphatase CD45 |
| Immunosuppression Profile | Phosphodiesterases | PDE4 |
| Immunosuppression Profile | Phosphodiesterases | acid spingomyelinase |
| Immunosuppression Profile | Cyclases | adenylyl cyclase (basal) |
| Immunosuppression Profile | Cyclases | adenylyl cyclase (stimulated) |
| Migraine | Cyclooxygenases | COX2 |
| Migraine | NO synthases | constitutive NOS (cerebellar) |
| Migraine | Monoamine & neurotransmitter synthesis & metabolism | GABA transaminase |
| Migraine | Cyclases | guanylyl cyclase (stimulated) |
| Pain | CMGC | ERK2 (42mapk) |
| Pain | Phospholipase | PLA2 |
| Pain | Cyclooxygenases | COXI |
| Pain | Cyclooxygenases | COX2 |
| Pain | AGC | PICA |
| Pain | Serine proteases | elastase |
| Pain | Metalloproteases | MMP-1 |
| Pain | Metalloproteases | MMP-2 |
| Pain | Metalloproteases | MMP-3 |
| Pain | Metalloproteases | MMP-7 |
| Pain | Phosphodiesterases | PDE4 |
| Pain | NO synthases | constitutive NOS (endothelial) |
| Pain | NO synthases | constitutive NOS (cerebellar) |
| Pain | Monoamine & neurotransmitter synthesis & metabolism | GABA transaminase |

-continued

| Therapeutic Target | Enzyme Family | Assay |
|---|---|---|
| Pain | Monoamine & neurotransmitter synthesis & metabolism | MAO-A |
| Pain | Monoamine & neurotransmitter synthesis & metabolism | MAO-B |
| Pain | Monoamine & neurotransmitter synthesis & metabolism | tyrosine hydroxylase |
| Pain | Miscellaneous enzymes | xanthine oxidase/superoxide O2-scavenging |

Figure 6A:
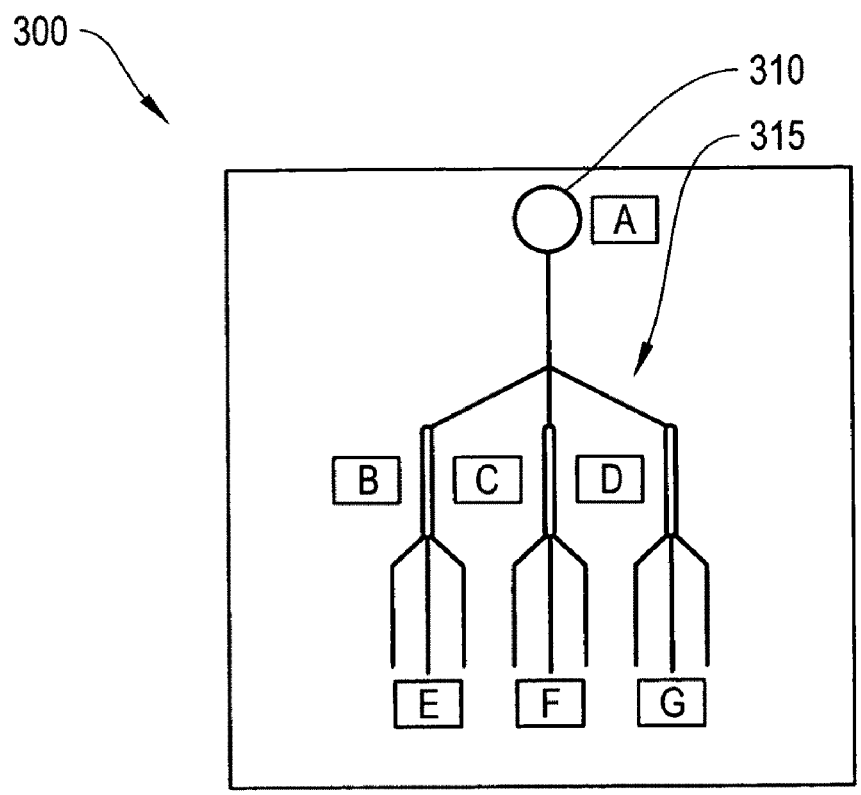
FIG. 6 presents an embodiment of a microfluidic device in accord with the present invention: a) microfluidic device with wells that lead to branched channels where cells flow and detect analytes within such channels; b) depiction of imaging fluorescence microfluidic device of 6a wherein black bars represent fluorescence in channels of the device visualized as an optical bar code.
Figure 6B:
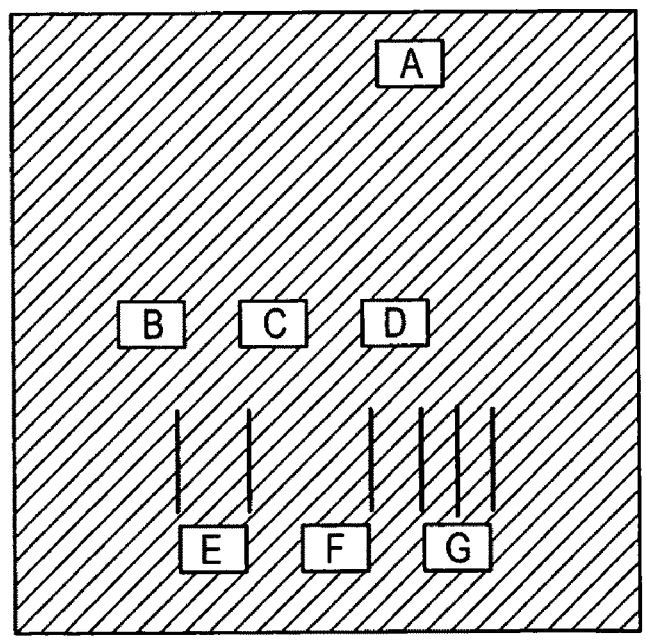

FIGS. 6a-b present another embodiment 300 of a sensor in accord with the present invention. The sensor comprises a well 310 and micro-channels, indicated generally at 315, branching successively therefrom. The cells are placed in the well 310, sensors with different specificities line each of the channels 315, and a solution is flowed from the well 310 through the channels 315. When the fluorescence from the channels 315 is imaged, the pattern formed by changes in intensity may be visualized as an optical barcode, as depicted in FIG. 6b, indicating the presence or absence of the various sensed materials in the solution.

The invention now being generally described, it will be more readily understood by reference to the following examples which are included merely for purposes of illustration of certain aspects and embodiments of the present invention, and are not intended to limit the invention in any way.

EXAMPLES

Ion-Selective Polymer Solution. The ion-selective polymer solution was made from the following components: 30 mg High Molecular Weight Polyvinyl Chloride, 60 mg Bis-2-Sebacate, 0.1 mg Sodium Ionophore X, 0.1 mg Sodium tetrakis[3,5-bis(trifluoromethyl)phenyl]borate, and 0.1 mg Chromoionophore I. The combined reagents were stirred in 500 µL of tetrahydrofuran (THF) to afford a homogenous solution.

Ion-Selective Sensor Fabrication. Quantum dots (ITK organic 655, Invitrogen) were flocculated in a methanol/isopropanol mixture with the addition of toluene in a 1:1 (v:v) ratio of toluene:quantum dot solution. The supernatant was removed and the quantum dots were resuspended in THF containing 3.3 mM 1-decanethiol. To the quantum dot solution (0.2 nMoles) was added the ion-selective polymer solution (17.2 nMoles Chromoionophore I, 50 µl) and the mixture was stirred.

Immobilized Polymer Matrix of Sensors. To form an immobilized polymer matrix of sensors, 1 µl of the polymer/quantum dot mixture was dropped onto a 5 mm glass coverslip to afford a thin homogenous matrix. Individual coverslips could then be placed in 96-well plates and experiments carried out.

Particle Sensors. To form particle sensors, dichloromethane was added to the polymer/quantum dot mixture in a 1:1 (v:v) ratio. This solution was then added directly to 5 mL of $H_2O$ containing 200 µg of dissolved 1,2-Diacyl-sn-Glycero-3-Phosphoethanolamine-N-[Methoxy(Polyethyleneglycol)-550] (PEG-lipid) by injecting through a pipette tip during sonication. Sonication was performed with a probe-tip sonicator (Branson) at 15% amplitude during and after addition for a total of 3 minutes, resulting in plasticized polymer nanosphere formation. The solution was then passed through a 0.2 µm syringe filter (Acrodisc, Gelman Laboratory) to remove large particles.

Particle Sizing and Zeta Potential. Particle size and zeta potential of the sensors were determined using a nanosizer (Nano Series ZS90, Malvern).

Figure 7:
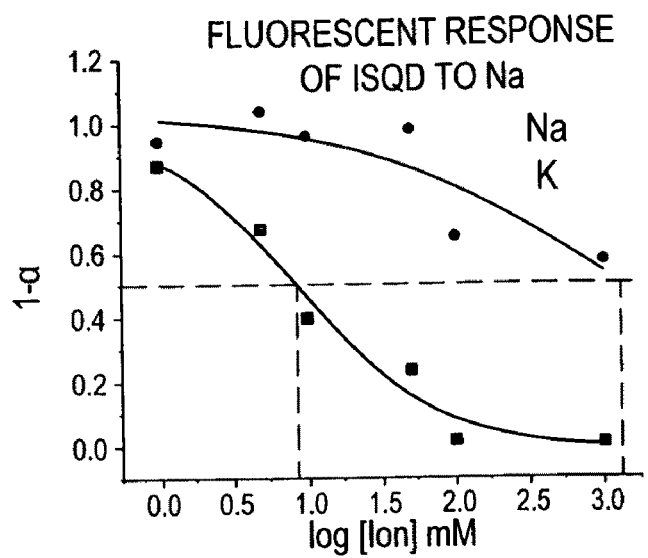
FIG. 7 shows the selectivity of the nanosensor of the invention for ion detection.

Calibration and Selectivity. Selectivity was determined using immobilized polymer matrix sensors. Parallel measurements were taken during addition of increasing ion concentration in HEPES (10 mM) buffered solution (pH=7.4) for response to sodium and potassium (n=4 each). Response was determined by expressing the data as $\alpha=(I-I_{min})/(I_{max}-I_{min})$. I is the intensity at the given ion concentration, $I_{min}$ is the intensity at the minimum signal (0 Na$^+$), and $I_{max}$ is the intensity at the maximum signal (1 M Na$^+$). Data were acquired in a Spectramax Gemini EM microplate fluorometer (Molecular Devices) exciting at 405 nm and emitting at 655 nm. The immobilized polymer matrix sensors were pretreated with HEPES buffered solution at pH=5.0, the pH of the sensors in solution. The baseline was then established in HEPES buffered solution at pH=7.4. Sodium and potassium solutions in the range of 1 mM to 1 M were added and the sensor was allowed to equilibrate before measurements were made. Response was determined by fitting a sigmoidal curve to the plot of α vs. ion concentration using Origin software, FIG. 7.

Figure 8A:
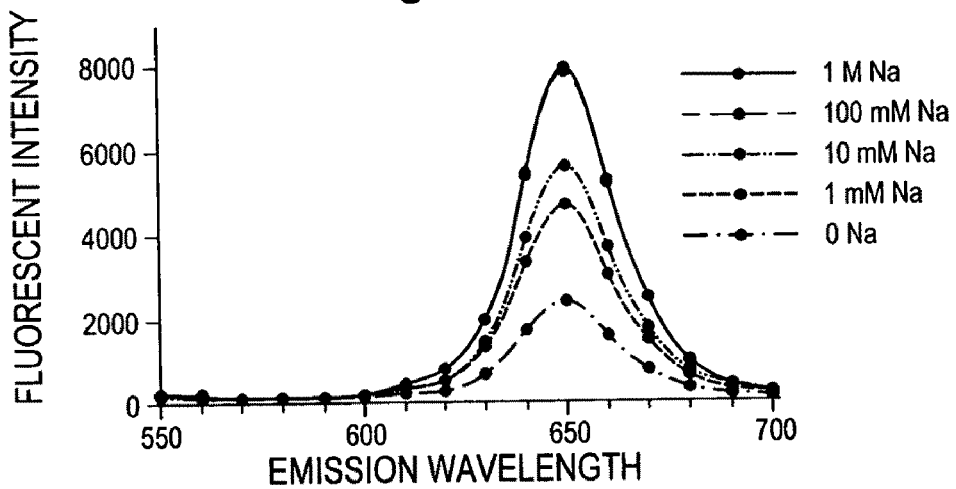
FIG. 8 depicts the experimental response to sodium. a) Spectral response of immobilized sensors to increasing concentrations of sodium. b) Calibration curve of ratiometric sensors.

In order to prevent dilution effects, the polymer matrix with no biocompatible coating was immobilized to a glass coverslip for calibration and selectivity measurements. The dynamic range of the sensor was found to be 1 mM to 1 M, shown spectrally in FIG. 8a. By adjusting the ratio of components, the concentration range was tuned to maximize the resolution at typical levels of intracellular sodium. In this case, the resolution was 80 µM at 17 mM, the center of the dynamic range. This means that a change in fluorescence intensity of 1% would correspond to a change in concentration of 80 µM, as measured on a fluorescence plate reader.

Figure 8B:
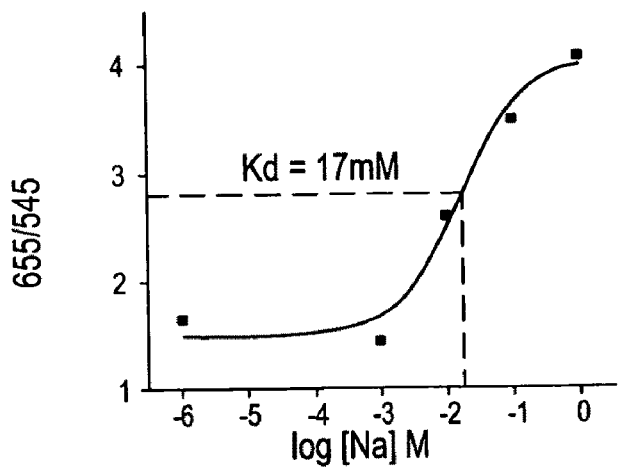

Ratiometric Measurements Immobilized polymer matrix sensors containing both 545 nm and 655 nm quantum dots was made in a similar fashion to the method described above. In this case, 1 nmole of each colored (i.e., emission wavelength) quantum dot was used, giving a total of 2 nmoles of quantum dots just as above. The sensors were calibrated with sodium ions while recording emission at 545 and 655 nm in the fluorometer, using an excitation wavelength of 405 nm. The ratio of 655/545 was taken, averaged over the data set and plotted using the graphing software program Origin. A sigmoidal curve was fit to the data and a half-maximal response was determined (FIG. 8b).

A control ion-selective polymer matrix was made similarly to polymer matrix described above, however the control polymer matrix did not contain Chromoionophore I. Immobilized polymer matrix sensors were made as described above. The response was determined by measuring fluorescence over 30 minutes after addition of 200 mM sodium solution. (This was performed in parallel with standard immobilized polymer matrix sensors to analyze the response time).

Spectral Overlap. Absorbance characteristics of the chromoionophore were obtained by creating sensors without quantum dots. The sensors were placed in a 96-well plate and absorbance was measured at wavelengths ranging from 500 nm to 700 nm. This was performed in the presence of 0, 1, 10, 100, and 1000 mM sodium solution in pH 7.4 Hepes buffer. From these spectral results, quantum dots were selected that emit fluorescence at a wavelength that coincides with the chromoionophore absorbance wavelengths. The overlap was confirmed by creating a sensor without chromoionophore but with quantum dots at the ratio mentioned above. A fluorescent spectrum was then measured by exciting at 400 nm and collecting emission from 600 nm to 700 nm in steps of 5 nm. In the absence of the chromoionophore, the quantum dot sensors fluoresced at an intensity that was not affected by the presence or absence of sodium ions.

Figure 9:
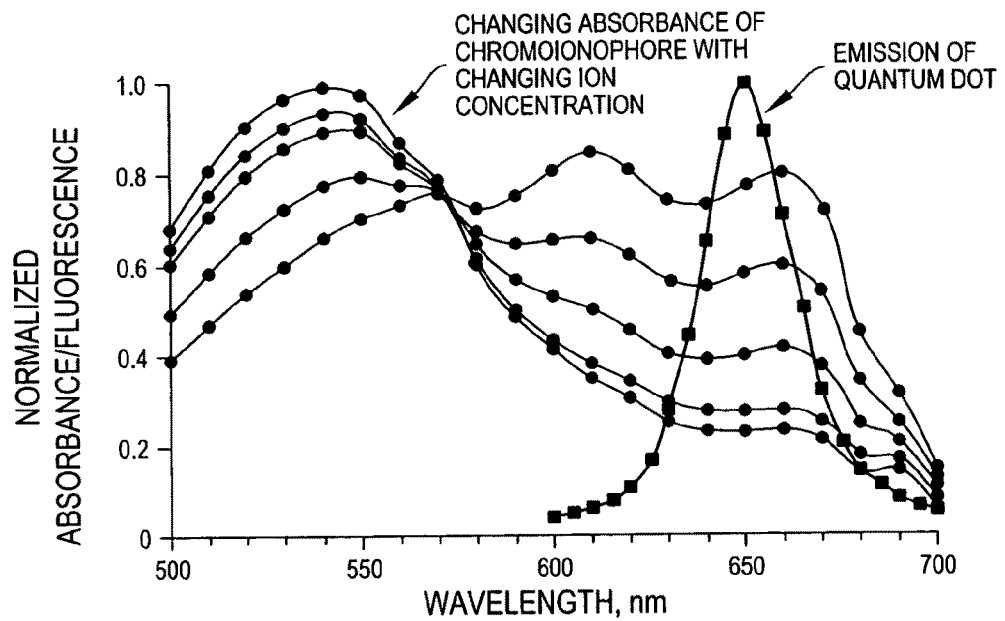
FIG. 9 depicts the spectral overlap of a quantum dot that fluoresces at 655 nm and the absorbance of a chromoionophore at varying sodium concentrations.

A quantum dot with fluorescence maximum at 655 nm and a chromoionophore in a sensor that absorbs fluorescence at low sodium ion concentrations is depicted in FIG. 9. The absorbance of the chromoionophore at 655 nm (gray lines, FIG. 9) decreases as sodium concentration increases, resulting in an increase in fluorescent signal directly related to increasing sodium concentration. Note the preferred overlap of the quantum dot emission (red line, FIG. 9).

Particle sensors without quantum dots: A polymer cocktail was formulated using, for example, traditional amounts of the sensor components (PVC, plasticizer, ionophore, chromoionophore and ionic additive) in a 1:1 (v:v) THF/dichloromethane solution. A probe-tip sonicator was used to sonicate an aliquot of 100 μL of polymer solution in 5 mL of buffer containing 0.1% PEG modified lipid. The nanosensors were dried by passing the particle solution through a nitrogen feed airbrush.

Surface Chemistry: The surface chemistry of the sensor can be changed by varying the concentration of the functionalized PEG incorporated onto the sensor. As above, zeta potential can be used to analyze the effectiveness of the coating at any given functionalized PEG concentration. The concentration of the functionalized PEG may be changed to optimize the properties of the sensors to their intended use.

Incorporation of Surface modifier onto Nanosphere Surface: The PEG lipid molecule PEG2000 PE {1,2-Dipalmitoyl-sn-Glycero-3-Phosphoethanolamine-N-[Methoxy(Polyethylene glycol)-2000](Ammonium Salt)} (Avanti Polar Lipids, Alabaster Ala.) can be used to attach functional groups. The amine functional group is also available through Avanti Polar Lipids, DSPE-PEG(2000)Amine {1,2-Distearoyl-sn-Glycero-3-Phosphoethanolamine-N-[Amino(Polyethylene Glycol)2000](Ammonium Salt)}, and requires no alterations.

The functionalized PEG can be dissolved into HEPES Buffered Saline (HeBS) and added to a solution containing sensor. The mixture may be mixed, e.g., with a vortexer for 1-2 minutes, to ensure ample interaction time and destabilization of aggregates. The resulting sensor-PEG can be subjected to acidification (decrease of solution pH from 7.4-5.5) and mechanical stress (trituration). The zeta potential can be measured (zetasizer) before and/or after acidification and mechanical stress to determine the surface concentration of the SM. This may correlate to the ability of the functionalized PEG to coat the surface of the sensor and withstand chemical and mechanical changes associated with the endocytotic pathway.

Biocompatibility. Biocompatibility was determined by incubating the sensors with HEK 293 cells (ATCC). The cells were trypsonized from normal culture and pipetted into a clear 96-well plate at a concentration of 30,000 cells/well. The cells were grown overnight in 300 μL of media to allow attachment to the plate. An aqueous solution (20 μL) containing $10^{11}$ particle sensors/mL was added to each well. For control experiments 20 μL of distilled water was used. Different particles were used to compare to the particle sensors. Particles used for comparison include: gold nanoparticles (colloidal gold 100 nm, SPI) and FluoSpheres (20 nm carboxylate modified microspheres, Invitrogen). Each type of nanosensor was tested on 8 wells of cells. The nanosensors were incubated with the cells overnight and the media was changed the following day.

Figure 10:
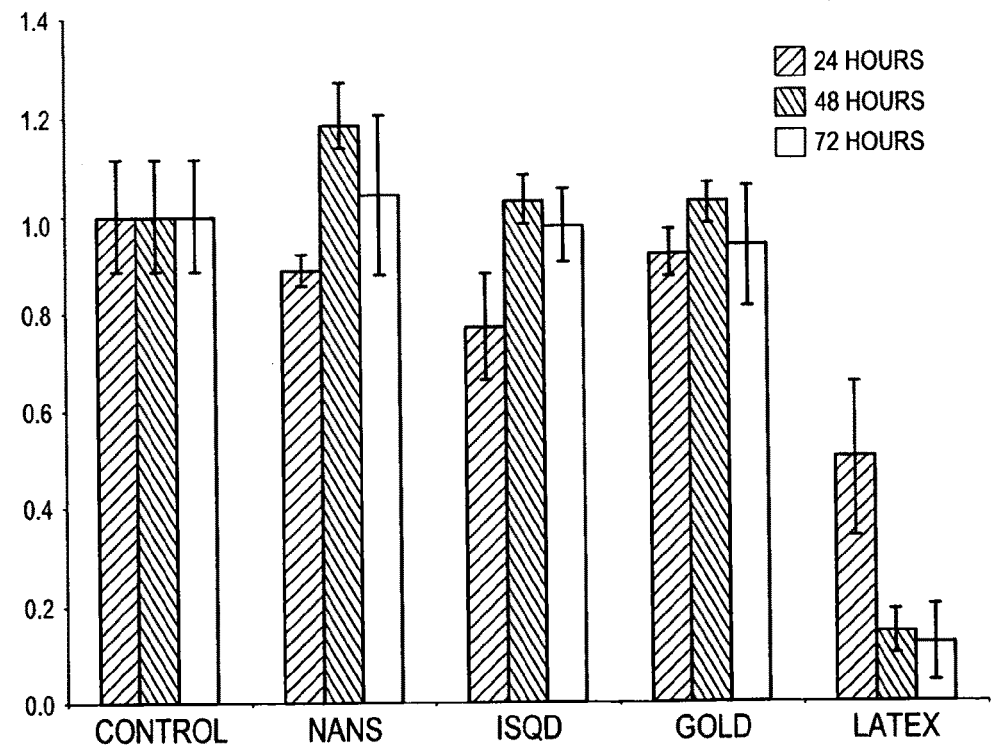
FIG. 10 depicts biocompatibility of nanosensors in HEK cells. HEK cells were incubated with either control (water), nanosensors without quantum dots (nans), quantum dot nanosensors, 100 nm gold nanoparticles, or 20 nm latex beads (a negative control).

At 24, 48, and 72 hours following washing, an MTT assay (3-(4,5-Dimethylthiazol-2-yl)-2,5-diphenyltetrazolium bromide) was performed (In vitro toxicology assay kit, Sigma). The cells were incubated with MTT for 2 hours. The MTT reduction product formazan was then dissolved and the absorbance of each well was read at 570 and 690 nm. The 690 nm absorbance served as background and was subtracted from the 570 nm value. The data was then averaged and compared to control to generate FIG. 10.

Figure 11:
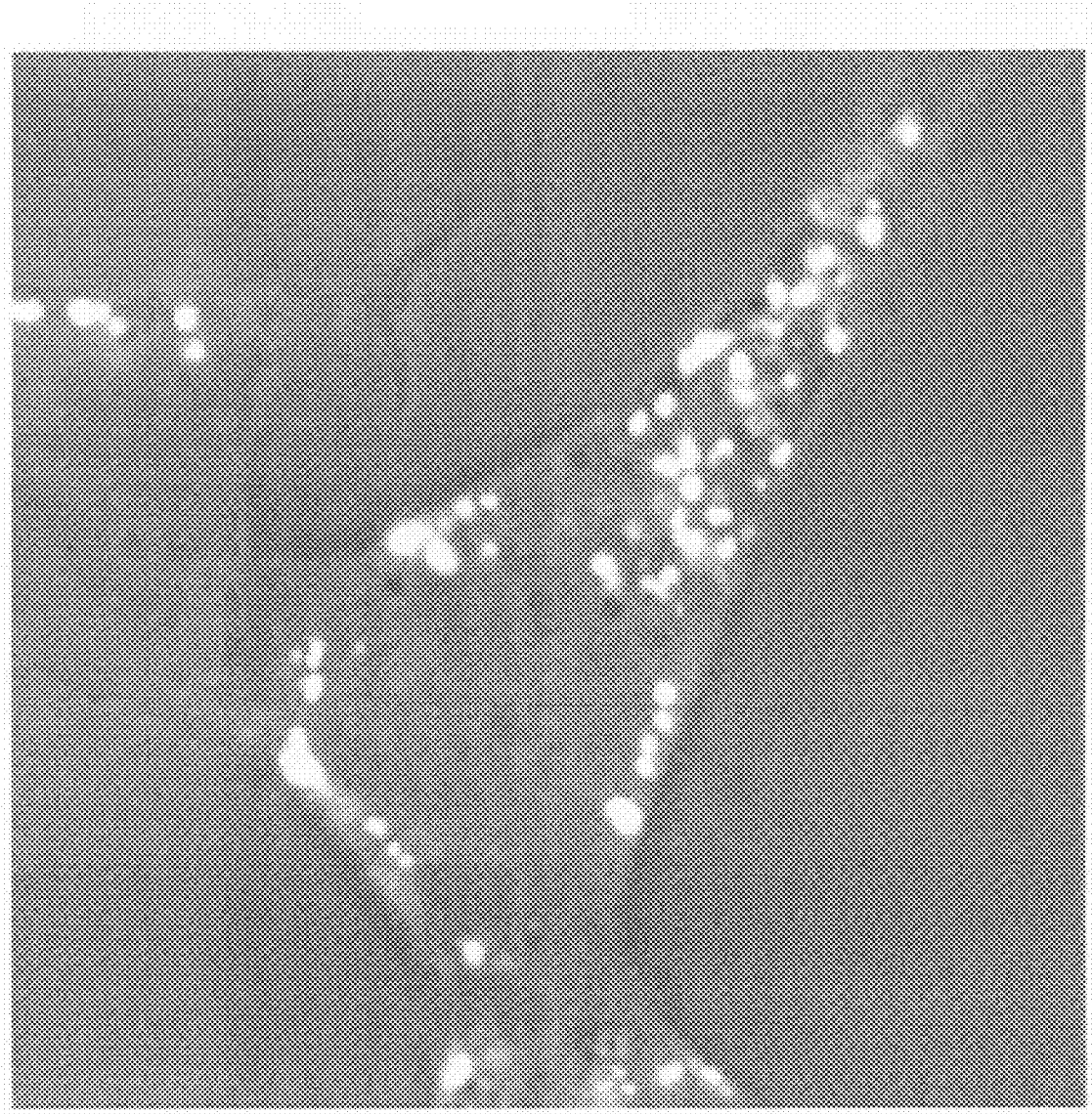
FIG. 11 is a confocal image of nanosensors without quantum dots loaded into an HEK 293 cell.

Loading sensors without quantum dots into cells: One method used for loading the cell involved incubating a solution of sensors in media with the cells overnight. The following day, the cells were washed 3× with PBS buffer. The cells were then imaged on the confocal microscope, with excitation 633 nm and emission 670-690 nm indicating that some of the polymer nanosensor had loaded into the cell, with plenty in the cytosol, but the image indicated a distribution in larger bundles clustered around the nucleus, FIG. 11.

Loading sensors into cells: A method for loading sensors into cells involves injecting the sensors into the cytosol of the HEK 293 cells via a 2 MOhm resistance patch pipette. The sensor solution may be diluted, e.g., one to one with a 2× intracellular solution. Once a GOhm seal has been achieved, the membrane ruptures and the sensors diffuse into the cytosol of the cell. No pressure need be applied to the patch pipette solution; rather the sensors enter the cytoplasm by simple diffusion. Time course experiments can be performed by acquiring sensor signal every minute over the course of 30 minutes to evaluate the rate of diffusion out of the patch pipette and homogeneity of distribution once inside the cytosol. Patching of cells is discussed in detail below.

Ability to Load into Cell: The sensors can be loaded into the test cell, such as HEK 293 or HL-1 cells. HEK 293 cells are maintained by standard cell culture and HL-1 cells are maintained similarly with alterations. Cells may be plated, e.g., onto 25 mm glass cover slips in 6 well plates at 25% confluence the day before experiments are to be carried out. When using HEK 293 cells the cover slips may be coated with poly-L-lysine, while cover slips for HL-1 cell experiments may be coated with gelatin and fibronectin.

The sensors in a HeBS solution may be added to 2 mL of cell culture media (at volumes not exceeding a ratio of 1:10) to replace the media in each well. The sensors can be incubated with the cells at 37° C. 5% $CO_2$, e.g., 10 min-24 hrs. Following incubation, the cover slips may be washed with HeBS containing 10 mM Glucose warmed to 37° C. and transferred to a microscope chamber. The chamber may be filled with HeBS with glucose and placed onto the microscope (microscope experiments may be performed on the LSCM). Data may be acquired using LSCM. Images may be acquired using a plan-apochromatic 63×1.4 NA oil immersion lens. Excitation/Emission settings may be selected according to the type of sensors being tested, e.g., for particle sensors-PEG Ex/Em of 633/670-690 nm. Loading may be evaluated by determining the quantity of sensors in each cell. A lack of nuclear loading may indicate either intracellular loading or plasma membrane incorporation.

Ability to Locate Into cytosol: The sensors may be analyzed for their ability to release from endosomes and enter the cytosol. Both HEK 293 and HL-1 cells may be prepared for microscopy according to the methods above. Additionally, the sensors may be loaded as described above, optionally with organelle-specific dyes. LSCM images may be acquired using the same microscope configuration described above. Cells may be loaded with sensors as described above and fixed for analysis of cytosolic location by TEM.

Imaging of sensors: After loading via patch pipette the sensors for both simultaneous patch experiments and independent imaging experiments may be performed. Images can be acquired with a standard CCD camera (CoolSnap HQ, Roper Scientific) or a high speed camera (Cooke, for channel experiments) attached to a Zeiss Axiovert 200 microscope. A standard FITC cube (Chroma) may be used when imaging CoroNa Green. Channel activity may be controlled with the patch setup and fluorescence detection may be timed to coordinate with channel opening.

Intracellular calibration: Calibration experiments can be performed in HEK 293 cells. The SENSORs can be calibrated in the cytosol after injection loading with a pipette. The sodium ionophore gramicidin (10 µM, Sigma) can be used to transport sodium across the membrane and Strophanthidin (100 µM, Sigma) can be used to deactivate any Na—K ATPase in the cells. Two solutions can be made that contain 140 mM Sodium (30 mM NaCl and 110 mM sodium gluconate) and zero Sodium (30 mM KCl and 110 mM potassium gluconate, to maintain ionic balance). Both solutions may also contain 10 mM HEPES, 10 mM glucose and, 1 mM EGTA (sigma) and a pH of 7.4. They can be mixed to achieve the desired concentration of sodium and perfused into the microscope chamber. Acquisitions of data may be made every 5 seconds and the sodium concentration may only be switched after a plateau in signal has been achieved for over two minutes. Selectivity can be determined by performing a calibration response to potassium. In this case, however, valinomycin (Sigma) may be used instead of gramicidin, all other conditions being the same.

Response repeatability can be determined using the conditions in the sodium calibration. The extracellular concentration of sodium can be switched back and forth from zero sodium to 50 mM sodium every ten minutes over the course of an hour.

Intracellular Response to Ion of Interest: Experiments may be performed to determine responsiveness of the nanosensors in the cytosol. Cells prepared for microscope experiments and functionalized nanosensors may be loaded as described above. Nanosensors may be imaged on a LSCM as described above. A description of methods suitable to characterize sodium nanosensor response follows; when using other ion-specific nanosensor, different ionophores can be employed.

LSCM images may be from nanosensor-loaded cells in HeBS containing zero sodium. A sodium ionophore such as Valinomycin (10 µM) (Sigma) may be added to equilibrate the concentration of sodium between the extracellular solution and the cytosol. Sodium concentrations may be increased in a step-wise manner by addition of a high sodium (1 M) stock HeBS. Images may be acquired after the system is allowed to reach equilibrium (~2-3 min) and intensity of the nanosensors can be measured. The sodium concentration may be raised, e.g., to 1 M, to establish a maximum concentration value of intensity. The data may then be correlated to the both the minimum intensity and maximum intensity and a calibration curve can be generated.

In a similar fashion, selectivity of the cytosolic nanosensor may be determined using interfering ions and their corresponding ionophores. The addition of interfering ions and the ionophore may be added while performing the calibration mentioned above. The acquired calibration curve may then be compared to that generated from sodium ion alone and a selectivity coefficient can be determined.

Nanosensor-loaded cells may also be subjected to whole-cell patch-clamp. The cells can be exposed to a drug to induce sodium flux across plasma membrane channels. Channel activity using patch-clamp can be recorded simultaneously with nanosensor fluorescence. This allows a direct comparison of this method to measure ion flux with the instant method discussed herein.

Whole Cell Patching: Recombinant HEK 293 cells expressing $Na_V1.7$ can be used to analyze sodium detection of intracellular nanosensors. Standard whole cell voltage clamp protocols may be employed to assess channel current density, voltage-dependent activation, inactivation, and the time course of recovery from inactivation. Ionic currents may be recorded with whole-cell voltage clamp methods, using an Axopatch-200B amplifier (Axon Instruments). Borosilicate glass electrodes with tip resistances 1-3 Mohm can be used. Command pulses may be generated by 12-bit digital-to-analog converter controlled by pCLAMP6 software (Axon Instruments). Experiments may be conducted at 36° C. To measure activity of the voltage-gated sodium channels, currents can be recorded following a step change of the holding potential from −120 mV to −20 mV test potential. The external solution may contain (mmol/L): 30 NaCl, 110 CsCl, 1.8 $CaCl_2$, 2 $CdCl_2$, 1 $MgCl_2$, 10 HEPES, 10 glucose, 1 4-AP. Intracellular solution may contain (mmol/L): 10 NaCl, 130 CsCl, 5 EGTA, 10 HEPES, 10 glucose. Inactivation and activation kinetics can be analyzed. Nanosensors may be introduced via patch pipette in the whole cell configuration, and maximum amplitude of the sodium current can be measured simultaneously with measurement of sodium flux optical recording from the nanosensors.

The same experiments may be repeated with recombinant $K_V$ 1.3 HEK 293 cells to demonstrate specificity of the sodium-sensitive nanosensors. In this case the cells may be hyperpolarized to below the reversal potential for potassium to allow for potassium influx into the cell. To measure the potassium currents, the extracellular solution may contain (mmol/L) NaCl 136, KCl 5.4, $MgCl_2$ 1, $CaCl_2$ 1, $NaH_2PO_4$ 0.33, HEPES 5, and dextrose 10 (pH 7.35, NaOH). For delayed rectifier current recording, nifedipine (5 µmol/L), 4-aminopyridine (2 mmol/L), and atropine (200 nmol/L) can be added to suppress L-type calcium current ($I_{Ca,L}$), transient outward current ($I_{to}$), and 4-aminopyridine-dependent muscarinic $K^+$ currents. Dofetilide (1 µmol/L) can be added for $I_{Ks}$ recording. For $I_{to}$ recording, nifedipine may be replaced by $CdCl_2$ (200 µmol/L). $Na^+$ current ($I_{Na}$) contamination may be avoided by substitution of equimolar Tris-HCl for NaCl and use of tetrodotoxin. A suitable internal solution for $K^+$-current recording may contain (mmol/L) K-aspartate 110, KCl 20, $MgCl_2$ 1, MgATP 5, LiGTP 0.1, HEPES 10, Na-phosphocreatinine 5, and EGTA 5.0 (pH 7.3, KOH).

Validation of sensor response with molecular dyes: The same experiments carried out on sensors may be performed using a fluorescein detection microscope cube. The cell impermeant CoroNa Green salt can be loaded through the patch pipette to determine if patch pipette loading alters the location and response of the dye.

Characterization of sensor function: Blockade of sodium channel using lidocaine and STX can reduce sodium flux into the cell, resulting in decrease in signal amplitude using optical recordings from the sensors. Recombinant $Na_V1.7$ HEK 293 cells may be subject to whole cell patch clamp, and the sensors may be introduced via the patch clamp. Lidocaine or STX may be perfused into the patch chamber and peak amplitude of the sodium current can be determined both by patch clamp (using standard voltage-dependent activation protocol) and optical recording (sensors) before and after infusion of the agent.

Figure 12:
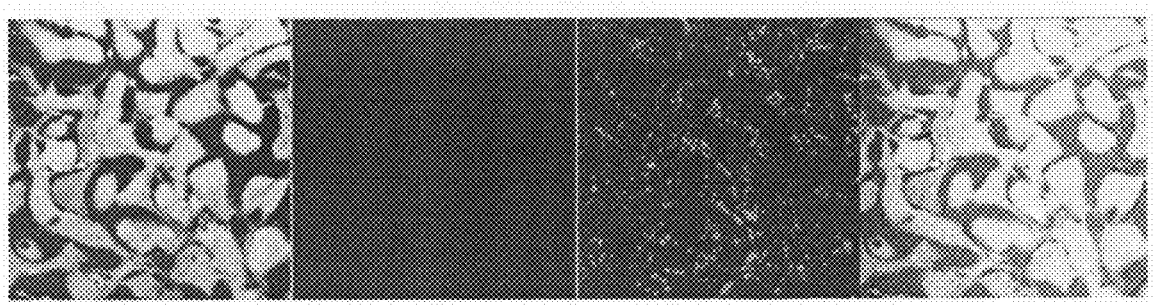
FIG. 12 shows a LIVE/DEAD assay wherein nanosensors with quantum dots were loaded into HEK 293 cells overnight and then stained. The green indicates healthy cells, while the red stains the nuclei of dead cells. No difference in the ratio of live to dead cells was noted between nanosensor loaded cells and control (no nanosensors).
Figure 13A:
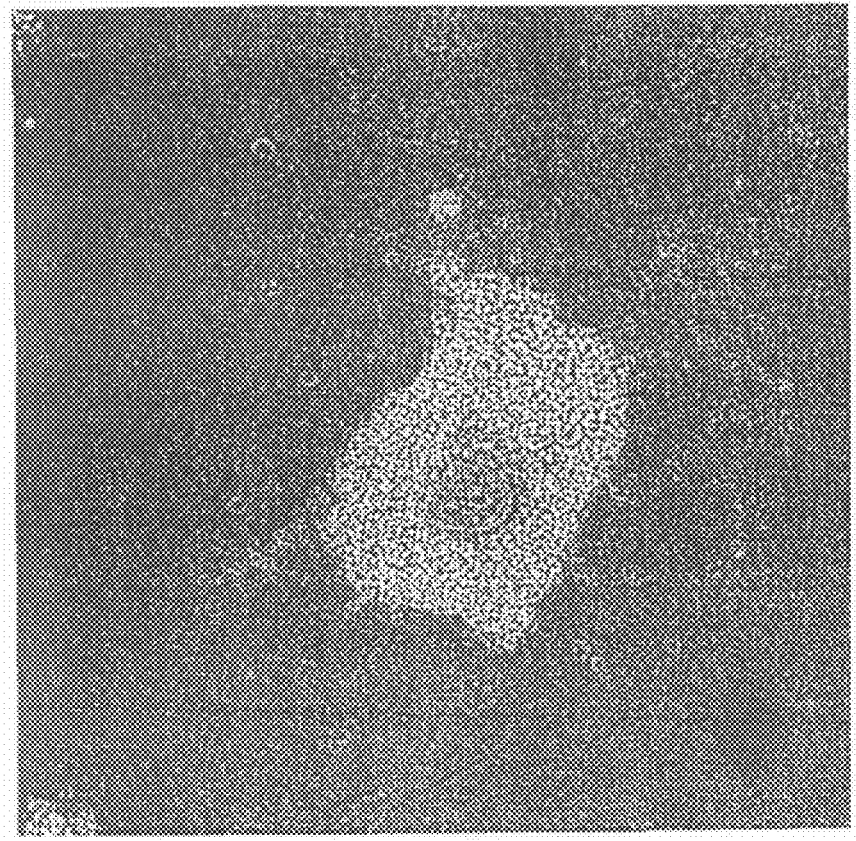
FIG. 13 depicts a. fluorescence image of an isolated neonatal rat ventricular myocyte loaded with sodium-selective nanosensors. b. the fluorescence collected from a nanosensor in a cardiac cell during stimulation

Live/Dead Assays After Nanosensor Loading: A fluorescence live/dead assay, consisting of calcein to stain living cells and ethidium bromide to stain the nuclei of dead cells, was performed in order to determine the viability of cells loaded with nanosensors, FIG. 12. The staining procedure included incubation of nanosensor-loaded cells (overnight loading, as above) in 8 μM of calcein and 8 μM of ethidium bromide for 20 minutes at 37° C. 5% $CO_2$, then rinsing 3×. The cells were then imaged on the confocal microscope. In FIG. 12 the green indicates healthy cells, while the red stains the nuclei of dead cells. No difference in the ratio of live to dead cells was noted between nanosensor loaded cells and control (no nanosensors). Following an implementation of this method, it was noted that the number of living cells was not different from control cells (not shown) which contained no nanosensors. Nanosensors in Cardiac Cells: Isolated neonatal rat ventricular myocytes were plated onto laminin coated 25 mm coverslips. Electroporation was performed in a custom chamber with custom parallel electrodes spaced at 1 cm. The cells were porated in a Ringer's solution containing 1:10 volume ratio of nanosensor solution. 800 V pulses were applied for 20 μseconds 8 times using an electroporator (Harvard Apparatus). The cells were then allowed to recover for 10 minutes before imaging. Images were taken on a confocal microscope (LSM 510 Meta, Zeiss) exciting at 488 nm and emitting at 650-690, 63× oil immersion objective. As can be seen in FIG. 13a, the nanosensors loaded into the cardiac cells efficiently using electroporation.

Figure 13B:
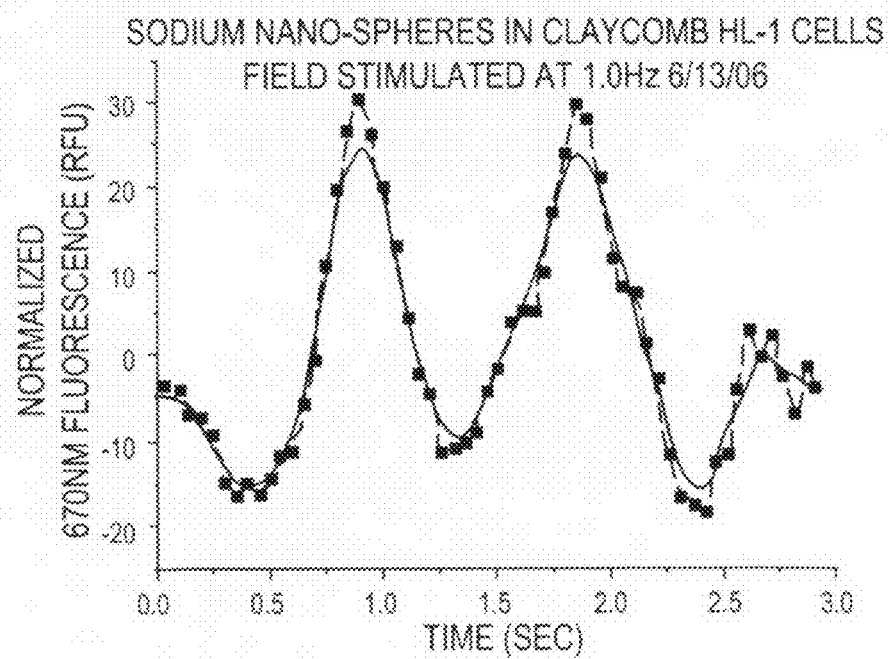

As the cells "beat" during electrical stimulation in cardiac cells, the fluorescence from the sodium sensors was collected and was seen to oscillate at 1 Hz, the pacing frequency. In FIG. 13b, the fluorescence collected from a nanosensor during stimulation, is charted. The changes of fluorescence observed are attributed to oscillation of sodium, as the changes occur at the pacing frequency of the cells. The data is the average of three time segments of the same experiment (data from time 0-3 seconds was averaged with data 3-6 seconds and data 6-9 seconds), and base-line corrected to account for photobleaching.

Those skilled in the art will recognize, or be able to ascertain using no more than routine experimentation, many equivalents to the specific embodiments of the invention described herein. Such equivalents are intended to be encompassed by the following claims.

The invention claimed is:

1. A sensor comprising one or more quantum dots, a polymer, an ionophore and a chromoionophore, wherein in an initial state photons emitted from the one or more quantum dots are absorbed by the chromoionophore, and when the ionophore associates with an ionic analyte, the chromoionophore stops absorbing photons emitted by the quantum dot.

2. A sensor comprising one or more quantum dots, a polymer, an ionophore and a chromoionophore, wherein in an initial state photons emitted from the one or more quantum dots are not absorbed by the chromoionophore, and when the ionophore associates with an ionic analyte, the chromoionophore absorbs photons emitted by the quantum dot.

3. An apparatus for measuring an ionic analyte within a living cell, the apparatus comprising:
(a) a sensor of claim 1 or 2; and
(b) circuitry for detecting the photons.

4. A method for manufacturing sensors according to claim 1 or 2 comprising:
combining an ionophore, a chromoionophore, quantum dots and a polymer in an organic solvent to form a suspension, and
adding the suspension to an aqueous liquid under conditions that promote the formation of nanoparticles.

5. A method for manufacturing sensors according to claim 1 or 2 comprising:
combining an ionophore, a chromoionophore, quantum dots and a polymer in an organic solvent to form a suspension,
placing the suspension on a surface, and
removing the organic solvent.

6. A method for detecting an ionic analyte of a living cell, the method comprising:
(a) contacting the cell with a sensor of claim 1 or 2,
(b) exciting the quantum dot with a light source causing the quantum dot to fluoresce, and
(c) detecting a signal from the sensor.

7. The sensor of claim 1 or 2, wherein the ionic analyte is $K^+$, $Na^+$, $Ba^{2+}$, $Li^+$, $NH_4^+$, or $Ca^{2+}$.

8. The sensor of claim 1 or 2, wherein the ionic analyte is $Cl^-$ or $NO_3^-$.

9. The sensor of claim 1 or 2, further comprising a surface modifier.

10. The sensor of claim 1 or 2, wherein the sensor comprises multiple quantum dots, chromoionophore and ionophore.

11. The sensor of claim 1 or 2, wherein the sensor is a film.

12. The sensor of claim 1 or 2, wherein the sensor is a nanoparticle.

13. The sensor of claim 9, wherein the surface modifier comprises a hydrophilic portion and a hydrophobic portion.

14. The sensor of claim 13, wherein the hydrophilic portion of the surface modifier is polyethylene glycol.

15. The sensor of claim 13, wherein the hydrophobic portion of the surface modifier is a lipid.

16. The sensor of claim 13, wherein the hydrophobic portion of the surface modifier and the hydrophilic portion of the surface modifier are bound together through a linker.

17. The sensor of claim 16, wherein the linker is a covalent bond, a phosphate or a ceramide.

18. The sensor of claim 12, wherein the diameter of the nanoparticle is between 5 nm and 300 nm.

19. The sensor of claim 12, wherein the diameter of the nanoparticle is between 20 nm and 200 nm.

20. The sensor of claim 12, wherein the nanosensor comprises only one quantum dot and has a diameter between 5 nm and 50 nm.

21. The method of claim 6, further comprising stimulating the cell so as to affect an ionic analyte.

22. The method of claim 6, wherein contacting the cell comprises placing at least one sensor in proximity to the cell.

23. The method of claim 6, wherein contacting the cell comprises coupling the at least one sensor to the exterior membrane of the cell.

24. The method of claim 23, wherein contacting the cell comprises coupling the at least one sensor to the exterior membrane of the cell proximate to an ion channel of the cell.

25. The method of claim 24, wherein the at least one sensor is coupled to the membrane via an antibody that specifically binds the ion channel.

26. The method of claim 6, wherein in one state the chromoionophore is deprotonated and in the second state the chromoionophore is protonated.

27. The method of claim 6, wherein the cell is in an animal.

28. The method of claim 6, wherein the fluorescence has an intensity indicative of the concentration of ionic analyte.

29. The method of claim 6, wherein the signal comprises the intensity of the fluorescence of the at least one sensor.

30. The method of claim 6, wherein the ionic analyte is $K^+$, $Na^+$, $Ba^{2+}$, $Li^+$, $NH_4^+$, or $Ca^{2+}$.

31. The method of claim 6, wherein the ionic analyte is $Cl^-$ or $NO_3^-$.

32. The method of claim 6, wherein contacting the cell comprises introducing the sensor into the cell.

33. The method of claim 6, wherein the sensor comprises multiple quantum dots, chromoionophore and ionophore.

34. The method of claim 21, wherein stimulating includes contacting the cell with at least one of a compound, a pathogen, a pharmaceutical compound, or a potential toxin.

35. The method of claim 26, wherein the ionic analyte is cationic and when ionic analyte is associated with the ionophore, the chromoionophore is deprotonated, and when the ionic analyte is not associated with the ionophore, the chromoionophore is protonated.

36. The method of claim 26, wherein the ionic analyte is anionic and when the ionic analyte is associated with the ionophore, the chromoionophore is protonated, and when the ionic analyte is not associated with the ionophore, the chromoionophore is deprotonated.

37. The method of claim 29, wherein detecting the signal comprises using a fluorometer.

38. The method of claim 32, wherein introducing the sensor into the cell comprises incubating the cell with the sensor in a medium.

39. The method of claim 33, wherein the sensor is a film.

* * * * *